United States Patent
Guo et al.

(10) Patent No.: US 6,486,201 B1
(45) Date of Patent: Nov. 26, 2002

(54) AGAROFUAN DERIVATIVES, THEIR PREPARATION, PHARMACEUTICAL COMPOSITION CONTAINING THEM AND THEIR USE AS MEDICINE

(75) Inventors: Jiyu Guo; Weijun Wang; Hongju Fang; Qian Liu; Wuyan Zhang; Dali Yin; Sujuan Sun; Ruiwu Liu; Chun Li; Haifan Liu; Donghui Wang, all of Beijing (CN)

(73) Assignee: Institute of Materia Medica, Chinese Academy of Medical Science (CN), Beijing (CN)

( * ) Notice: Subject to any disclaimer, the term of this patent is extended or adjusted under 35 U.S.C. 154(b) by 0 days.

(21) Appl. No.: 09/856,125
(22) PCT Filed: Nov. 19, 1999
(86) PCT No.: PCT/CN99/00196
§ 371 (c)(1),
(2), (4) Date: May 18, 2001
(87) PCT Pub. No.: WO00/31058
PCT Pub. Date: Jun. 2, 2000

(30) Foreign Application Priority Data

Nov. 19, 1998 (CN) .......................................... 98122447

(51) Int. Cl.$^7$ .................. C07D 307/00; A61K 31/343; A61P 25/22
(52) U.S. Cl. ........................................ 514/468; 549/459
(58) Field of Search ........................... 549/459; 514/468

(56) References Cited

FOREIGN PATENT DOCUMENTS

CH           608 187         12/1978

OTHER PUBLICATIONS

Huffman, et al, 1982, J. Org. Chem, 47(17), 3254–8.*

Liu, Qian et al., "Studies of the Synthesis of Baimuxinol By Catalytic Hydrogenation of Dehydrobaimuxinol", Chinese Chemical Letters, vol. 3, No. 7, pp. 495–498, 1992.

Maheshwari, M.L. et al., "Structure and Absolute Configuration of Norketoagarofuran, 4–Hydroxydihydroagarofuran...", Tetrahedron, vol. 19, pp. 1519–1525, 1963.

Huffman, John W., "Synthesis of Agarofurans by Cyclization of 10–Epieudesmene–3,11–diols", J. Org. Chem., 47, pp. 3254–3258, 1982.

* cited by examiner

Primary Examiner—Joseph K. McKane
Assistant Examiner—Andrea D. Small
(74) Attorney, Agent, or Firm—Burns, Doane, Swecker & Mathis, L.L.P.

(57) ABSTRACT

The compound represented by formula (I), in which the substitutes are defined as in the specification and the claims, or their stereoisomers, the process for preparing them, pharmaceutical composition containing them and their use as medicine.

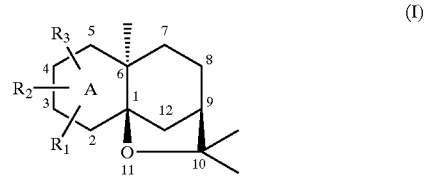

(I)

19 Claims, No Drawings

AGAROFUAN DERIVATIVES, THEIR PREPARATION, PHARMACEUTICAL COMPOSITION CONTAINING THEM AND THEIR USE AS MEDICINE

This application is a 371 of PCT/CN99/00196 Nov. 19, 1999.

THE FIELD OF THE INVENTION

This invention relates to a series of new agarofuran derivatives, their preparation and pharmaceutical composition containing the same as well as pharmaceutical use thereof, particularly for the treatment of anxiety and/or depression.

BACKGROUND

Anxiety is a disease of human central nervous system (CNS) and its incidence is increasing in pace with the increasing competition of the society.

Anxiolytics were reported to be best sales among the CNS medication including benzadiazepine compounds (diazepam etc.), buspirone and fluoxetine. But,some of the side effects and defects have been observed such as resistance, addiction, relapse dr slow effect. So it is necessary to develop new anti-anxiety drugs which have better curative effect and lower unwanted effects.

Agarofuran compounds are contained in Aquillaria agallocha Roxb in which 9 compounds as follows have been reported in the following publications.

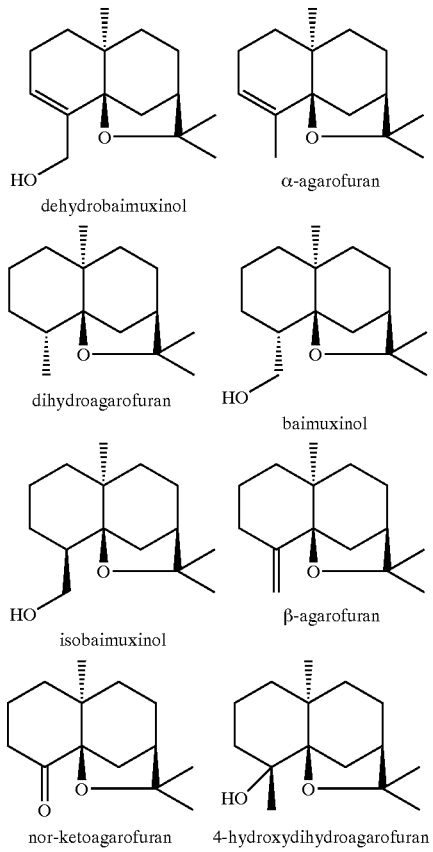

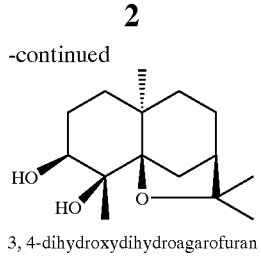

3, 4-dihydroxydihydroagarofuran

Tetrahedron 1963, 19, 1079 (M. L. Maheshwari); Tetrahedron 1963, 19, 1519 (M. L. Mheshwari); Tetrahedron 1965, 21, 115 (K. R. Varma); Phytochemistry 1984, 23, 2068 (K. Yoneda); Phytochemistry 1984, 23, 2066 (T. Nakamish); Acta Pharmaceutica Sinica 1986, 21, 516 (J-S, Yang); Acta Pharmaceutica Sinica 1989, 24,.264 (J-S, Yang); J. Am Chem. Soc. 1967, 89, 5665(H. C. Barret); J. Org. Chem. 1968, 33, 435 (J. A. Marshall); Tetrahedron, 1968, 24, 4917 (C. H. Heathcock); Can. J. Chem. 1968, 46, 2817 (A. Asselin); J. Org. Chem. 1979, 44, 546(G. Buchi); Chinese Chem. Lett. 1991, 2, 425(Q. Liu); Chinese Chem. Lett. 1992, 3, 495 (Q. Liu); J. Org. Chem. 1982, 47, 3254 (J. W. Huffman). All of the reports above were only concerned with chemistry of the compounds without teaching or mentioning their bioactivity.

THE OBJECT OF THE INVENTION

The aim of this invention is to find new anxiolytics, which have better efficacy and lower toxicity.

This invention has made discovery of the following new agarofuran compounds, which have therapeutic effects, particularly anti-anxiety effect, with better safety profile.

SUMMARY DESCRIPTION OF THE INVENTION

The first aspect of the invention relates to compounds of the formula (I) and/or stereoisomers thereof

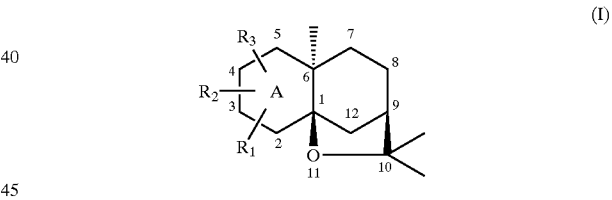

(I)

wherein
a double bond may or may not exist in A ring at position 2–3 or position 3–4; $R_1$, $R_2$ and $R_3$ are respectively at position 2, 3 or 4. $R_1$ and $R_2$ or $R_2$ and $R_3$ are independently at position 2, 3, or 4.

$R_1$ is H, $C_{2-12}$ straight or branched alkyl chain, saturated or unsaturated, for unsaturated chain, it may include 1–3 double bonds; the above defined alkyl may be unsubstituted or substituted by one or more substituents such as hydroxyl or carbonyl, said alkyl may also be substituted with cycloalkyl, heterocycle containing one or more heteroatoms or aryl group in which aryl is unsubstituted or substituted by one or more substitutent such as straight or branched $C_1$–$C_4$ alkyl, alkoxyl, halogen, trihalomethyl, amino, hydroxyl, nitro or N,N-dialkylamino; in the above definition, heterocycle is saturated or unsaturated mono-ring or poly-ring containing at least one heteroatom selected from oxygen, sulfur or nitrogen; aryl includes phenyl and naphthyl; the substituent may be at any possible position of the alkyl.

$R_2$ is H, oxo, hydroxyl, $C_1$–$C_{12}$ straight or branched alkyl chain, saturated or unsaturated, for unsaturated chain, it may include 1–3 double bonds, the above defined alkyl may be unsubstituted or substituted by one or more substituents such as hydroxyl or carbonyl, said alkyl may also be attached with cycloalkyl, heterocycle containing one or more heteroatoms or aryl group in which ary is unsubstituted or substituted by one or more substituent such as straight or branched $C_1$–$C_4$ alkyl, alkoxyl, halogen, trihalomethyl, amino, hydroxyl, nitro or N,N-dialkylamino; In the above definition, heterocycle is saturated or unsaturated mono-ring or poly-ring having at least one heteroatom selected from oxygen, sulfur or nitrogen; aryl includes phenyl and naphthyl; the substituent may be at any possible position of the alkyl.

$R_3$ is H, oxo, hydroxyl or halogen.

Provided that, $R_1$, $R_2$, and $R_3$ are not H at the same time.

According to the present invention, the compounds of the formula (I) exhibit prominent anti-anxiety activity which is characterized by its fast action, longer duration, lower dosage, higher safety coefficient and accompanied by anti-depression effect.

The another aspect of the invention provides a pharmaceutical composition comprising as active ingredient at least one compound of formula (I) or stereoisomer thereof and a pharmaceutical carrier or excipient.

The invention further includes the compound of formula (I) or composition containing it useful for prevention or treatment of anxiety and/or depression.

The invention further provides a method for prevention and/or treatment of anxiety—depression, which comprises administrating at least one compound of formula (I) or composition containing the same to host who needs prevention and/or treatment.

According to the present invention, compounds of formula (I) have exhibited anti-anxiety activity in elevated plus maze test and social interaction test on rat which are typical pharmacological model for axiolytics. Furthermore, a compound of formula (I) showed antidepressant activity in forced swimming test of mice which is typical pharmacological model for anti-depressants.

DETAILED DESCRIPTION OF THE INVENTION

Specifically, the invention relates to agarofuran derivatives of formula (I) and their stereoisomers,

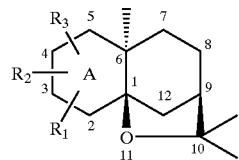

(I)

wherein a double bond may or may not exist in A ring at position 2–3 or position 3–4; $R_1$, $R_2$ and $R_3$ are respectively at position 2, 3 or 4. $R_1$ and $R_2$ or $R_2$ and $R_3$ are independently at position 2, 3, or 4.

$R_1$ is H, $C_{2-12}$ straight or branched alkyl chain, saturated or unsaturated, for unsaturated chain, it may include 1–3 double bonds; the above defined alkyl may be unsubstituted or substituted by one or more substituents such as hydroxyl or carbonyl, said alkyl may also be substituted with cycloalkyl, heterocycle containing one or more heteroatoms or aryl group in which aryl is unsubstituted or substituted by one or more substitutent such as straight or branched $C_1$–$C_4$ alkyl, alkoxyl, halogen, trihalomethyl, amino, hydroxyl, nitro or N,N-dialkylamino; in the above definition, heterocycle is saturated or unsaturated mono-ring or poly-ring containing at least one heteroatom selected from oxygen, sulfur or nitrogen; aryl includes phenyl and naphthyl; the substituent may be at any possible position of the alkyl.

$R_2$ is H, oxo, hydroxyl, $C_1$–$C_{12}$ straight or branched alkyl chain, saturated or unsaturated, for unsaturated chain, it may include 1–3 double bonds, the above defined alkyl may be unsubstituted or substituted by one or more substituents such as hydroxyl or carbonyl, said alkyl may also be attached with cycloalkyl, heterocycle containing one or more heteroatoms or aryl group in which ary is unsubstituted or substituted by one or more substituent such as straight or branched $C_1$–$C_4$ alkyl, alkoxyl, halogen, trihalomethyl, amino, hydroxyl, nitro or N,N-dialkylamino; In the above definition, heterocycle is saturated or unsaturated mono-ring or poly-ring having at least one heteroatom selected from oxygen, sulfur or nitrogen; aryl includes phenyl and naphthyl; the substituent may be at any possible position of the alkyl.

$R_3$ is H, oxo, hydroxyl or halogen.

Provided that, $R_1$, $R_2$, and $R_3$ are not H at the same time.

According to the present invention, a preferred group of compounds of formula (I) is indicated as formula (Ia), wherein there is a double bond in A ring at position 2–3; $R_1$ is defined as above and at position 2; $R_2$ and $R_3$ are H, provided that $R_1$ is not H.

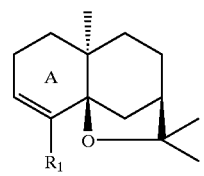

(Ia)

According to the present invention a preferred group of compound of formula (I) is indicated as formula (Ib), wherein there is no double bond in A ring; $R_1$ and $R_2$ are both at position 2, wherein $R_1$ is as previously defined; $R_2$ is H or OH, $R_3$ is H, provided that $R_1$ is not H.

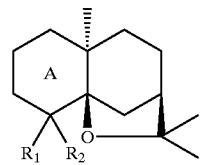

(Ib)

According to the present invention, a preferred group of compounds of formula (I) is indieated as formula (Ic), wherein there is no double bond in A ring; $R_1$ is at position 2; $R_2$ and $R_3$ are both at position 3 in A ring; $R_1$, $R_2$ and $R_3$ are as previously defined, provided that $R_1$ and $R_2$ are not hydrogen at the same time.

(Ic)

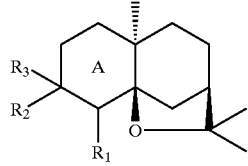

According to the present invention, a preferred group of compounds of formula (I) is indicated as formula (Id) in which there is a double bond at position 3–4 in A ring; wherein $R_2$ is at position 2, $R_2$ is a $C_{1-12}$ straight or branched alkyl chain, saturated or unsaturated, for unsaturated chain, it may include 1–3 double bonds; the above defined alkyl may be unsubstituted or substituted by one or more substituent such as substituents such as hydroxyl or carbonyl, it may also be attached with cycloalkyl, heterocycle containing one or more heteroatoms or aryl group in which aryl is unsubstituted or substituted by one or more substituent such as straight or branched $C_1$–$C_4$ alkyl, alkoxyl, halogen, trihalomethyl, amino, hydroxyl, nitro or N,N-dialkylamino; in the above definition, heterocycle is saturated or unsaturated mono-ring or poly-ring having at least one heteroatom selected from oxygen, sulfur or nitrogen; aryl includes phenyl and naphthyl; the substituent may be at any possible position of the alkyl $R_1$ and $R_3$ are H.

(Id)

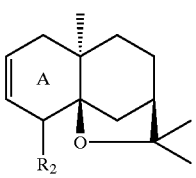

According to the present invention, a preferred group of compounds of formula (I) is indicated as formula (Ie) in which there is a double bond at position 2–3 in A ring and $R_2$ is at position 3 ; wherein $R_2$ is a $C_{2-12}$ straight or branched alkyl;, chain, saturated or unsaturated; for unsaturated chain, it may include 1–3 double bonds; the above defined alkyl may be unsubstituted or substituted by hydroxyl or carbonyl; it may also be attached with cycloalkyl, heterocycle containing one or more heteroatoms or aryl group in which aryl is unsubstituted or substituted by one or ore substitutent such as straight or branched $C_1$–$C_4$ alkyl, alkoxyl, halogen, trihalomethyl, amino, hydroxyl, nitro or N,N-dialkylamino; in the above definition, heterocycle is saturated or unsaturated mono-ring or poly-ring having at least one heteroatom selected from oxygen, sulfur or nitrogen; aryl includes phenyl and naphthyl; the substituent may be at any possible position of the alkyl.

$R_1$ and $R_3$ are H.

(Ie)

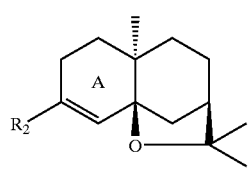

A particularly preferred group of compounds of formula (1) is as follows:

(1R,6S,9R)6,10,10-Trimethyl-2-propyl-11-oxatricyclo[7.2.1.0$^{1,6}$]dodec-2-ene;

(1R,6S,9R)6,10,10-Trimethyl-2-butyl-11-oxatricyclo[7.2.1.0$^{1,6}$]dodec-2-ene;

(1R,6S,9R)6,10,10-Trimethyl-2-pentyl-11-oxatricyclo[7.2.1.0$^{1,6}$]dodec-2-ene;

(1R,6S,9R)6,10,10-Trimethyl-2-hexyl-11-oxatricyclo[7.2.1.0$^{1,6}$]dodec-2-ene;

(1R,6S,9R)6,10,10-Trimethyl-2-isopentyl-11-oxatricyclo[7.2.1.0$^{1,6}$]dodec-2-ene;

(1R,6S,9R)6,10,10-Trimethyl-2-benzyl-11-oxatricyclo[7.2.1.0$^{1,6}$]dodec-2-ene;

(1R,6S,9R)6,10,10-Trimethyl-2-(4-fluorobenzyl)-11-oxatricyclo[7.2.1.0$^{1,6}$]dodec-2-ene;

(1R,6S,9R)6,10,10-Trimethyl-2-(3-hydroxypropyl)-11-oxatricyclo[7.2.1.0$^{1,6}$]dodec-2-ene;

(1S,2R,6S,9R)6,10,10-Trimethyl-2-butyl-11-oxatricyclo[7.2.1.0$^{1,6}$]dodecane;

(1S,2S,6S,9R)6,10,10-Trimethyl-2-butyl-11-oxatricyclo[7.2.1.0$^{1,6}$]dodecane;

(1R,2S,6S,9R)6,10,10-Trimethyl-2-butyl-2-hydroxy-11-oxatricyclo[7.2.1.0$^{1,6}$]dodecane;

(1R,2R,6S,9R)6,10,10-Trimethyl-2-butyl-11-oxatricyclo[7.2.1.0$^{1,6}$]dodecane;

(1R,6S,9R)6,10,10-Trimethyl-2-butylidene-11-oxatricyclo[7.2.1.0$^{1,6}$]dodecane;

(1S,2S,6S,9R)6,10,10-Trimethyl-2-(3-hydroxypropyl)-11-oxatricyclo[7.2.1.0$^{1,6}$]dodecane;

(1S,2R,6S,9R)6,10,10-Trimethyl-2-butyl-11-oxatricyclo[7.2.1.0$^{1,6}$]dodecane;

(1S,2S,3S,6R,9R)6,10,10-Trimethyl-2-butyl-3-hydroxy-11-oxatricyclo[7.2.1.0$^{1,6}$]dodecane;

(1S,2R,6R,9R)6,10,10-Trimethyl-2-butyl-11-oxatricyclo[7.2.1.0$^{1,6}$]dodec-3-one;

(1S,3S,6R,9R)6,10,10-Trimethyl-3-butyl-3-hydroxy-11-oxatricyclo[7.2.1.0$^{1,6}$]dodecane;

(1R,1'R,6S,9R)6,10,10-Trimethyl-2-(1-hydroxybutyl)-11-oxatricyclo[7.2.1.0$^{1,6}$]dodec-2-ene;

(1R,1'S,6S,9R)6,10,10-Trimethyl-2-(1-hydroxybutyl)-11-oxatricyclo[7.2.1.0$^{1,6}$]dodec-2-ene;

2-Butyryl(1R,6S,9R)6,10,10-Trimethyl-11-oxatricyclo[7.2.1.0$^{1,6}$]dodec-2-ene;

Methyl(1R,6S,9R)6,10,10-Trimethyl-11-oxatricyclo[7.2.1.0$^{1,6}$]dodec-2-ene-2-ethyl ketone;

(1S,6R,9R)6,10,10-Trimethyl-3-butyl-11-oxatricyclo[7.2.1.0$^{1,6}$]dodec-2-ene;

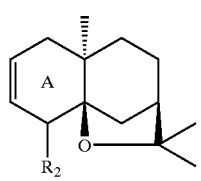

In the present invention, compounds of formula (Ia)–(Ie) may be prepared by reaction scheme I–V

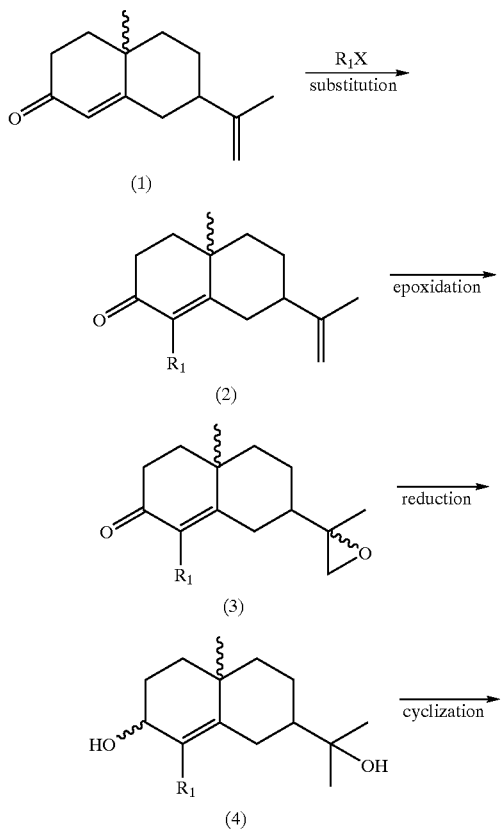

Wherein $R_1$ is as previously defined, X is halogen.

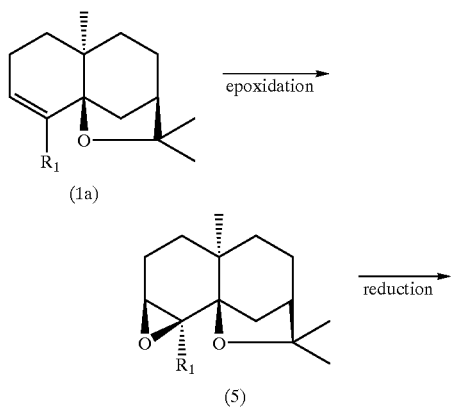

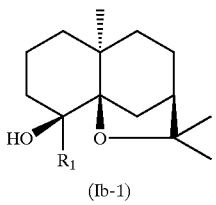

Where compound of formula (Ib-1) is a specific kind of formula (Ib) wherein $R_1$ is as previously defined; $R_2$ is β-OH, or

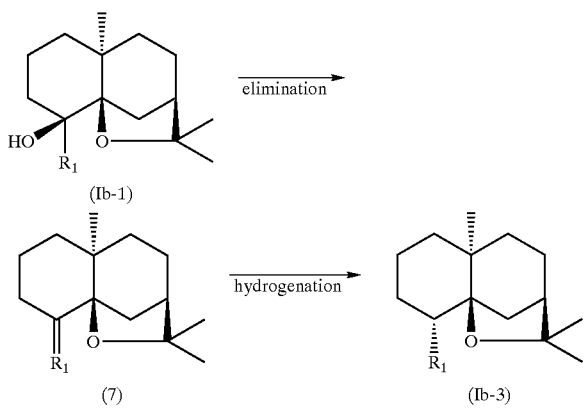

Where compound of formula (Ib-2) is a specific kind of formula (Ib) wherein $R_1$ is as previously defined, $R_2$ is α-OH, or Where compound of formula (Ib-3) is a specific kind of formula (Ib) wherein $R_1$ is as previously defined and at α-position, $R_2$ is H, or

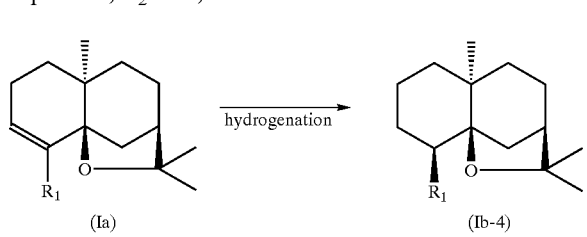

Where compound of formula (Ib-4) is a specific kind of formula (Ib) wherein $R_1$ is as previously defined and at β-position, $R_2$ is H.

Scheme III

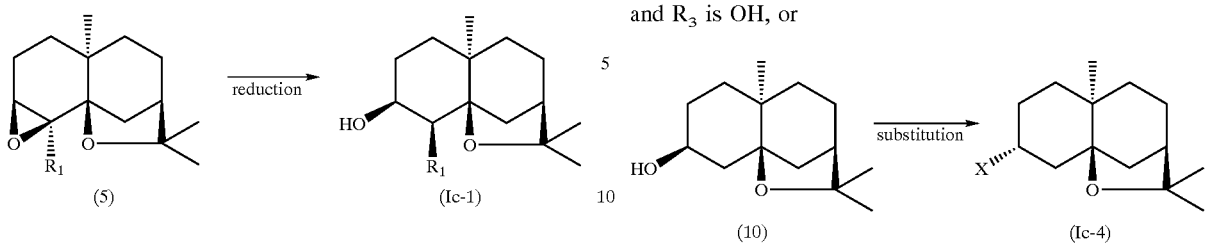

Where compound of formula (Ic-1) is a specific kind of formula (Ic) wherein $R_1$ is as previously defined, $R_2$ is H, and $R_3$ is OH, or

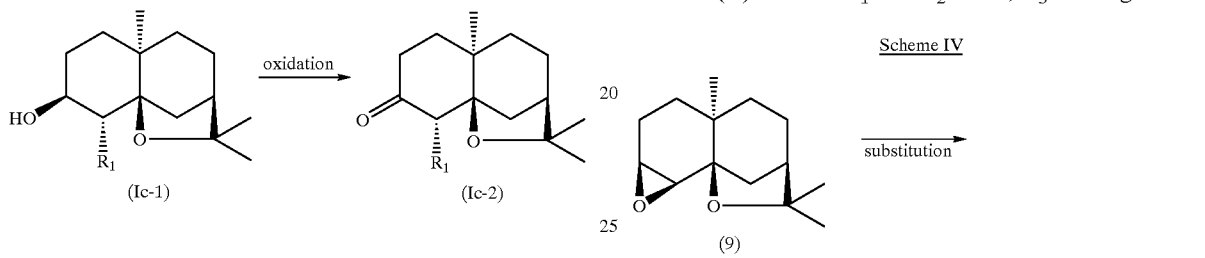

Where compound of formula (Ic-2) is a specific kind of formula (Ic) wherein $R_1$ is as previously defined, $R_2$ and $R_3$ are oxygen, or

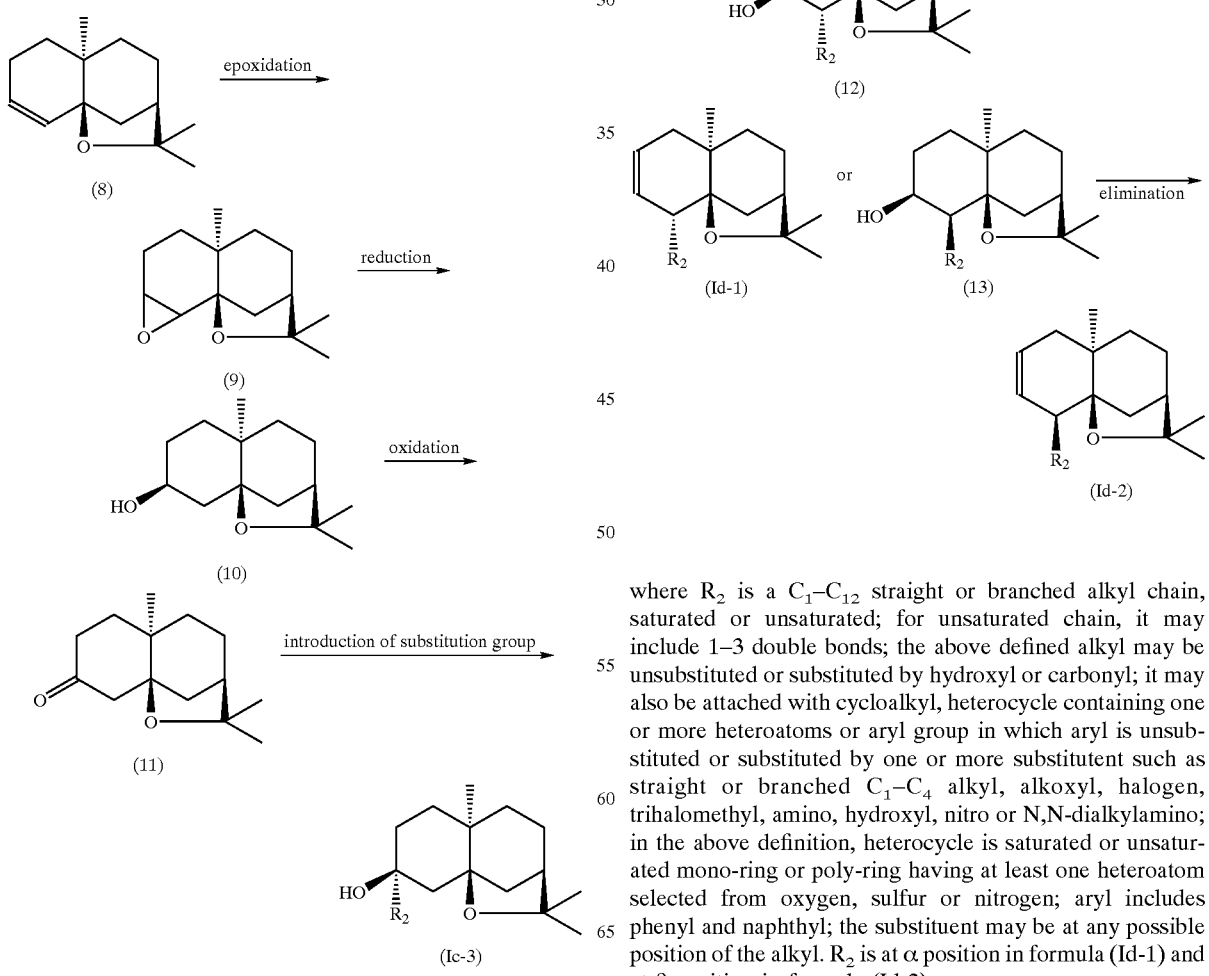

Where compound of formula (Ic-3) is a specific kind of formula (Ic) wherein $R_2$ is as previously defined, $R_1$ is H, and $R_3$ is OH, or Where compound of formula (Ic-4) is a specific kind of formula (Ic) wherein $R_1$ and $R_2$ are H, $R_3$ is halogen.

Scheme IV where $R_2$ is a $C_1$–$C_{12}$ straight or branched alkyl chain, saturated or unsaturated; for unsaturated chain, it may include 1–3 double bonds; the above defined alkyl may be unsubstituted or substituted by hydroxyl or carbonyl; it may also be attached with cycloalkyl, heterocycle containing one or more heteroatoms or aryl group in which aryl is unsubstituted or substituted by one or more substitutent such as straight or branched $C_1$–$C_4$ alkyl, alkoxyl, halogen, trihalomethyl, amino, hydroxyl, nitro or N,N-dialkylamino; in the above definition, heterocycle is saturated or unsaturated mono-ring or poly-ring having at least one heteroatom selected from oxygen, sulfur or nitrogen; aryl includes phenyl and naphthyl; the substituent may be at any possible position of the alkyl. $R_2$ is at α position in formula (Id-1) and at β-position in formula (Id-2).

Scheme V

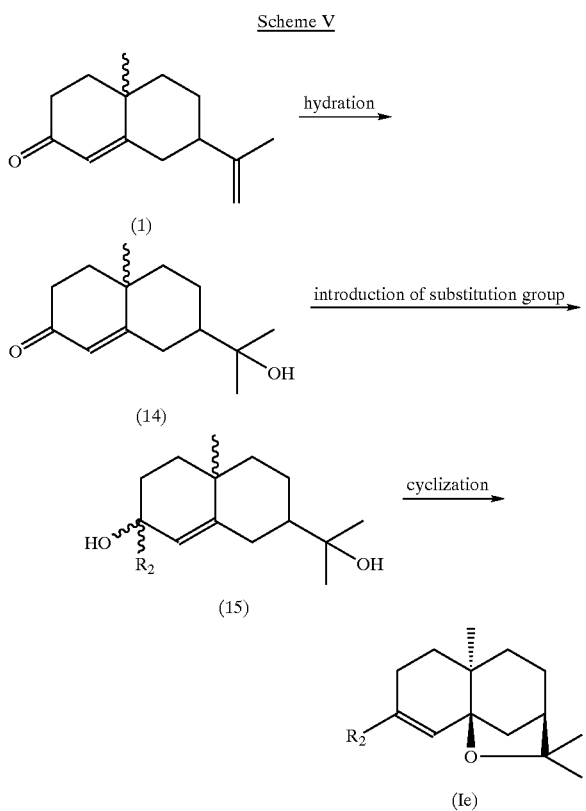

Wherein $R_2$ is a $C_{1-12}$ straight or branched alkyl chain, saturated or unsaturated; for unsaturated chain, it may include 1–3 double bonds; the above defined alkyl may be unsubstituted or substituted by hydroxyl or carbonyl; it may also be attached with cycloalkyl, heterocycle containing one or more heteroatoms or aryl group in which aryl is unsubstituted or substituted by one or more substitutent such as straight or branched $C_1$–$C_4$ alkyl, alkoxyl or groups such as halogen, trihalomethyl, amino, hydroxyl, nitro or N,N-dialkylamino; in the above definition, heterocycle is saturated or unsaturated mono-ring or poly-ring having at least one heteroatom selected from oxygen, sulfur or nitrogen; aryl includes phenyl and naphthyl; the substituent may be at any possible position of the alkyl.

In Scheme 1, (6R/S,9R)6-methyl-9-(1-methylvinyl)-bicyclo[4.4.0]deca-1-ene-3-one (formula 1) reacts with alkyl halide $R_1X$ ($R_1$ is as previously defined but not H, X is halogen) in the presence of alkaline medium in organic solvent, such as benzene, t-butanol of any other organic solvent that does not interfere with the reaction, to form (6R/S,9R)2-$R_1$-6-methyl-9-(1-methylvinyl)bicyclo[4.4.0] dec-1-ene-3-one (formula 2). The reaction is generally conducted at reflux temperature of the solvent used and the preferable alkaline reagents are metallic alkoxide or hydride such as sodium hydride and potassium t-butoxide. Reaction of compound of formula (2) with organic peracid, preferably meta-chloro-perbenzoic acid, to form (6R/S,9R)2-$R_1$-6-methyl-9-(1-methyl-epoxyethyl)bicyclo[4.4.0]-dec-1-ene-3-one (3). The reaction are conducted generally in organic solvents such as methylene chloride, chloroform, diethylether or any other solvent that does not interfere with the reaction, and at room temperature or lower temperature. Reduction of compound (3) with reducing agents such as metal hydride complex, preferably lithium aluminum hydride, to form compound of formula (4). The reactions are generally conducted at room temperature or lower temperature in organic solvent such as diethylether, tetrahydrofuran, methylene chloride, chloroform, benzene or any other solvent that does not interfere with the reaction. Compound (4) is converted to compound of formula (Ia) by treatment with acid, preferably inorganic acid, such as hydrochloric acid, sulfuric acid, or phosphoric acid and the reaction is generally conducted in solvents such as water, methanol, ethanol, diethylether, benzene, toluene, methylene chloride, chloroform, ethylacetate, tetrahydrofuran or a mixture thereof, preferably benzene-water, diethylether-water system at room temperature or lower temperature.

In Scheme II, compound of formula (Ia) is reacted with organic peracid, preferably meta-chloroperbenzoic acid, to form compound of formula (5) in organic solvent such as diethylether, methylene chloride, chloroform, benzene or any other solvent that does not interfere with the reaction at room temperature or lower temperature. The compound (5) thus formed is reduced by metal hydride complex or borane, such as $LiAlH_4$/Lewis acid, preferably $LiAlH_4$ or $LiAlH_4$/$AlCl_3$, to form compound of formula (Ib-1). The reaction is conducted in organic solvent such as diethylether, tetrahydrofuran or any other solvent that does not interfere with the reaction at room temperature or cooled with ice bath. (1R,6R,9R)6,10,10-trimethyl-11-oxatricyclo[7.2.1.0] dodecean-2-one (formula 6) reacts with organometallic reagent such as Grignard reagent or organolithium reagent to form compound of formula (Ib-2). The reaction can be conducted in organic solvent such as diethylether, tetrahydrofuran or any other solvent that does not interfere with the reaction at room temperature or cooled with ice bath or ice-salt mixture. Compound of formula (Ib-1) can be converted to compound of formula (7) when treated with thionyl chloride, phosphorus oxychloride, phosphorus pentoxide in 44 pyridine, or triethylamine at room temperature, or cooled with ice bath or ice-salt mixture. Catalytic hydrogenation of (7) to form compound of formula (Ib-3). The hydrogenation is catalyzed by generally used catalysts such as platinum oxide, Raney Ni, palladium on carbon, or rhodium on carbon etc. in organic solvent such as ethanol, methanol, acetic acid or any other solvent that does not. interfere with the reaction at room temperature. Similarly, catalytic hydrogenation of compound of formula (Ia) forms compound of formula (Ib-4) and the reaction is catalyzed by generally used catalysts such as platinum oxide, Raney Ni, palladium on carbon, or rhodium on carbon etc. in organic solvent such as ethanol, methanol, acetic acid or any other solvent that does not interfere with the reaction at room temperature.

In Scheme III, compound of formula (5) is reduced by metallic hydride complex, preferably LiAlH4, to form compound of formula (Ic-1) in organic solvent such as diethylether, tetrahydrofuran, 1,2-dimethoxyethane, or any other solvent that does not interfere with the reaction at room temperature. Oxidation of compound of formula (Ic-1) by $CrO_3$/pyridine, pyridinum chlorochromate (PCC) or Jones reagent, preferably PCC, produces compound of formula (Ic-2) and the reaction is generally conducted in organic solvent such as methylene chloride, chloroform, benzene or any other solvent that does not interfere with the reaction at room temperature or heated. (1S,6S,9R)6,10,10-trimethyl-11-oxatricyclo[7.2.1.0$^{1,6}$]dodec-2-ene (formula 8) is oxidized by organic peracid, preferably meta-chloroperbenzoic acid, to form (1S,2S,6R,9R)6,10,10-trimethyl-2,3-epoxy-11-oxatricyclo[7.2.1.0$^{1,6}$]dodecane (formula 9) and the reaction is conducted in organic solvent such as diethylether, methylene chloride, chloroform, benzene or any other solvent that does not interfere with the reaction at room temperature or cooled. The thus produced compound (9) is reduced by metallic hydride complex, preferably LiAlH$_4$ to form (1S,3S,6R,9R)6,10,10-trimethyl-11-oxatricyclo[7.2.1.0$^{1,6}$]dodecan-3-one (formula 10) and the reaction is conducted in organic solvent such as diethylether, tetrahydrofuran, 1,2-dimethoxyethane or any other solvent that does not interfere with the reaction at room temperature or cooled with ice bath. Compound of formula (10) is oxidized by CrO$_3$/pyridine, PCC, or Jones reagent, preferably PCC to form (1S,6R,9R)6,10,10-trimethyl-11-oxatricyclo[7.2.1.0$^{1,6}$]dodecan-3-one (formula 11 ) and the reaction is conducted in organic solvent such as methylene chloride, chloroform, benzene or any other solvent that does not interfere with the reaction at room temperature or heated. Compound (11) is reacted with organometallic reagent such as Grignard reagent or organolithium reagent to form compound of formula (Ic-3) and the reaction is conducted in organic solvent such as diethylether, tetrahydrofuran or any other solvent that does not interfere with the reaction at room temperature or cooled with ice bath. Compound of formula (10) react with phosphorous trihalide in the presence of triphenylphosphine to form (1S,3R,6R,9R)6,10,10-trimethyl-3-halo-11-oxatricyclo[7.2.1.0$^{1,6}$]dodecane and the reaction is conducted in anhydrous diethylether and cooled with ice bath or ice-salt mixture.

In Scheme IV, compound (9) reacts with Grignard reagent to form compound of formula (12) and the reaction is usually carried out in diethylether, tetrahydrofuran or any other solvent that does not interfere with the reaction at room temperature or cooled with ice bath. Treatment of compound of formula (12) with pyridine/thionyl chloride to eliminate a molecule of water produces compounds of formula of (Id-1) and (Id-2) and the reaction is carried out at room temperature or cooled with ice bath or ice-salt mixture.

Compound of formula (13) may be prepared following the similar method for preparation of compound of formula (Ic-1).

In Scheme V, treatment of (6R/S,9R)-6-methyl-9-(1-methylvinyl)-bicyclo[4,4,0]dec-1-ene-3-one (1) with mixture of sulfuric acid and formic acid at room temperature produces (6R/S,9R)-6methyl-9-(1-hydroxyisopropyl)-bicyclo[4.4.0]-dec-1-ene-3-one (14). Compound (14) reacts with organometallic reagent such Grignard reagent or organolithium reagent to form compound of formula (15) and the reaction is conducted in diethylether, tetrahydrofuran or any other solvent that does not interfere with the reaction at room temperature or cooled with ice bath or ice-salt mixture. Cyclization of compound of formula (15) to form compound of formula (Ie) is carried out in acidic medium, optionally with inorganic acid such as hydrochloric acid, sulfuric acid, or phosphoric acid in any solvent that does not interfere with the reaction such as water, methanol, ethanol, diethylether, benzene, toluene, methylene chloride, chloroform, ethylacetate, tetrahydrofuran, or a mixture thereof, particularly benzene-water, diethylether-water mixture. The reaction temperature is usually room temperature or lower.

In this invention, the term "alkyl", unless otherwise indicated, refers to straight or branched carbon chain with 2 to 12 carbon atoms, such as ethyl, propyl, isopropyl, n-butyl, isobutyl, tert-butyl, n-pentyl, iso-pentyl, neo-pentyl, 1-methybutyl, n-hexyl, isohexyl, heptyl, octyl, nonyl, or decyl and sail alkyl may be unsubstituted or substituted by hydroxyl or carbonyl on the chain.

In this invention, the term "halogen" refers to as fluoro, chloro, bromo, or iodo.

The term "unsaturated alkyl", unless otherwise indicated, refers to straight or branched carbon chains which contain 2 to 12 carbon atoms and 1 to 3 double bond in it, for example vinyl, 2-propenyl, 3-butenyl, 2-butenyl, 2-pentenyl, 3-pentenyl. Said unsaturated alkyl may be unstubstituted or substituted by hydroxyl or oxo. Compound of formula (I) may contain chiral centers of S or R configuration., therefore may have stereoisomers. The invention includes all the possible enantiomers and diastereomers, both mixtures and separated individual isomers. The mixture of two enantiomers, that is levo and dextro, may exist in different ratio. If there is cis, trans isomer, the invention includes the cis, trans isomers or the mixture thereof. The individual stereoisomer may be prepared by conventional resolution method or by stereoselective synthesis. If there is active H, the invention may also include tautomers.

Compound of formula (I) and their stereoisomers have showed activity on experimental anti-anxiety tests, therefore may be used as anxiolytic for living creature, particularly for mammals, especially for human being.

This invention also provides pharmaceutical composition comprising at least one active compound of formula (I) and/or its stereoisomer, or a pharmaceutically acceptable salt thereof as well as conventional pharmaceutically excipient or adjuvant. The composition 0.1%~90% by weight a compound of formula (I) or a pharmaceutically salt thereof and is prepared by the known method in this field. For this purpose, it may combine compound of formula (I) with one or more solid of liquid excipient and/or adjuvant, to make proper administration or dosage form for use in medicine or veterinary medicine.

The compounds represented by the general formula (1) are administrated alone or in the form of a pharmaceutical composition containing the same, administration route may be intestinal or parenteral, such as oral, intramuscular, subcutaneous, transdermally, intransally, intraperitoneally, rectally, topically, and the like. Said pharmaceutical preparations are formulated. by using usually used diluents such as fillers, bulking fillers, binders, wetting agents, disintegrants, surface active agents, lubricants; or excipients. The pharmaceutical preparations can be selected from various administration forms in accordance with the therapeutic purposes. As to typical administration forms, there can be exemplified tablets, pills, powders, liquids, suspensions, emulsions, granules, capsules, suppositories, injection preparations (liquids, suspensions, etc.), slowly releasing preparation, preparation form controlling release and the like. For the purpose of shaping the administration unit form into the tables, various carriers which are well-known in this field can be widely used. As to the examples of carriers, excipients such as lactose, white sugar, sodium chloride, glucose, urea, starch, calcium carbonate, kaolin, crystal-line cellulose, aluminum silicate and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrants such as dry starch, sudium alginate, agar-agar powder, laminaran powder, sodium hydrogencarbonate, calcium carbonate, polyoxyethylene sorbitan fatty acid esters, sodium laurylsulfate, monoglyceride of stearic acid, starch, lactose and the like; disintegration inhibitors such as white sugar, stearin, cacao butter, hydrogenated oils and the like; absorption accelerators such as quaternary ammonium salts, sodium laurylsulfate and the like; wetting agents such as glycerin, starch and the like; adsorbents such as starch, lactose, kaolin, bentonite, colloidal silicic acid and the like; lubricants such as refined talc, strearates, boric acid powders, polyethylene glycols and the like can be mentioned. The tablets preparations can be further shaped into tablets coated with usual tablet coating, for example sugar coated tablets, gelatin film coated tablets, tablets coated with enteric coating, tablets coated with film coating, or double layer tablets and multiple layer tablets. For the purpose of shaping the administration unit into pills, various carriers which are well-known in this field can be widely used. As to the examples of carriers, excipients such as glucose, lactose, starch, cacao butter, hydrogenated vegetable oils, kaolin, talc and the like; binders such as powdered acacia, powdered tragacanth, gelatin, ethanol and the like can be exemplified. For the purpose or shaping the administration unit into suppositories, various carriers which are well-known in this field can be widely used. As to the examples of carries, polyethylene glycols, cacao butter, higher alcohols, esters of higher alcohols, gelatin, semi-synthesized glycerides and the like can be mentioned. For the purpose of shaping the administration unit form into capsules, the compounds of formula (I) as the effective ingredient is mixed with the above-mentioned various carriers and the mixture thus obtained is placed into rigid gelatin capsules or soft capsules. For the purpose of shaping the administration unit into injection preparations, liquid preparations, emulsion preparations and suspension preparations are sterilized, further these preparations are preferably isotonic to the blood, and the all diluents which are conventionally used in this field can also be used for example, water, ethyl alcohol, macrogols, propylene glycol, ethyoxylated isostearyl alcohol, polyoxylated isostearyl alcohol, polyoxyethylenesorbitan fatty acid esters can be used. Additionally, for the purpose to prepare isotonic injection solutions, an adequate amount of sodium chloride, glucose or glycerin may be added to the injection preparations, further, usual dissolving additives, buffering agents, local anesthetics and the like may be added. Moreover, if necessary, coloring agents, preservatives, spices, flavors, sweetening agents and others may be added to the pharmaceutical preparations.

Dose of pharmaceutical preparation of the present invention is suitably selected depend on the usage, age of the patient, distinguish of sex and other conditions, and degree of the symptom, and generally the daily amount of effective compound of formula (I) may be about 0.001 to 100 mg/about 75 kg of the body weight per day, preferably about 0.01 to 20 mg. The above preparation may be administrated in single dose or to be divided into several dose such two, three or four dose.

The following example and biological activity test are used to illustrate this invention, but does not mean any limitation to the invention.

Starting materials used are known compounds or can be prepared by the known methods.

Preparation A (6R/S,9R)6-Methyl-9-(1-methylvinyl)-bicyclo[4.4.0]dec-1-ene-3-one

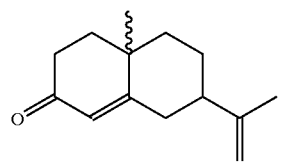

Step A: Preparation of Dehydrocarvone

Dihydrocarvone is prepared following the procedure described in J. Chem. Soc. Perkin I 1973, 19–23, 2109–2112.

Step B: Preparation of (1R/S,6R/S,9R)6-Methyl-9-(1-methylvinyl)-1-hydoxy-bicyclo[4.4.0]decan-3-one

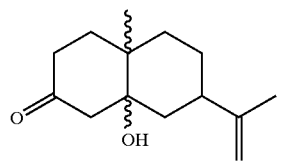

This compound is prepared following the procedures described in J. Am. Chem. Soc. 1974, 96(26), 8102–8106.

Step C: (6R/S,9R)6-Methyl-9-(1-methylvinyl)-bicyclo[4.4.0]dec-1-ene-3-one

To a solution of 30 g (0.135 mol) of compound obtained from procedure B in 90 mL of methanol is added 10% NaOH under protection of nitrogen. The reaction mixture is heated to reflux for 1 hour, then cooled to room temperature, and neutralized with 3 N HCl. After removal of solvent in vacuo, the water layer is extracted with ethylacetate, and the combined organic layer is washed with saline, and dried. After removal of solvent, the residue is separated by vacuum chromatography (VLC) and washed with petroleum ether/ethyl acetate (40/1–10/1) to give product as oil. MS: 204 (M+). $^1$H NMR (CDCl$_3$, δ): 1.30 (s, 3 H, 6-CH$_3$), 1.74 (s, 3 H, 10-CH$_3$), 4.76 (br. S, 1 H, 10-CH$_2$), 5.77 (d, J=3.6 Hz, 1 H, 2-H).

Preparation B

3-Bromopropyl Tetrahydropyranyl Ether

Step A: 3-Bromopropanol

To a suspension of 1.5 g (39 mmol) of LiAlH$_4$ in 100 mL of anhydrous diethylether cooled to −70° C. is added 11.45 g (63 mmol) of bromopropionic acid ethyl ester. The reaction mixture is stirred at −60° C. for 2 hours, then warmed to −10° C. in 30 min. The reaction is quenched with water saturated diethylether, then add 10% NaOH. After filtration, the filtrate is dried and evaporated to dryness to give 6.8 g of product in 70% yield.

Step B: 3-Bromopropyl Tetrahydropyranyl Ether

To a solution of 5.8 g (42 mmol) of 3-bromopropanol prepared in step B and 3.5 g (42 mmol) of dihydropyran in 15 mL of methylene chloride is added 20 mg (0.116 mmol) of p-toluenesulfonic acid, and the reaction mixture is stirred at room temperature for 7 hours, then washed with 10% NaOH solution and brine, dried, and evaporated to dryness to give 8.7 g of title product in 96% yield.

Preparation C (1R,6R,9R)6,10,10-Trimethyl-11-oxatricyclo[7.2.1.0$^{1,6}$]dodec-2-ene

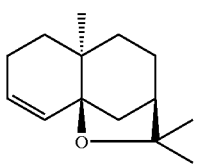

Step A: (6R/S,9R)6-Methyl-9-(1-methylepoxyethyl)bicyclo[4.4.0]dec-1-ene-3-one

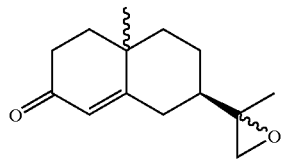

A mixture of 8 g (0.039 mol) of (6R/S,9R)6-methyl-9-(1-methylvinyl)bicyclo[4.4.0]dec-1-ene-3-one obtained from preparation A, 23 g (0.0416 mol) of m-chloroperbenzoic acid (55% content) and 100 mL of methylene chloride is stirred at room temperature for 4 hours, then washed with 1 N NaOH solution and brine, dried, and evaporated to dryness to give 9 g of crude product.

Step B: (3R/S,6R/S,9R)6-Methyl-9-(1-methyl-1-hydroxyethyl)bicyclo[4.4.0]dec-1-ene-3-ol

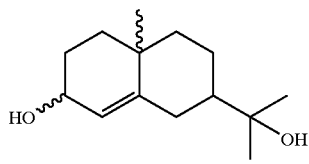

To a mixture of 4 g (0.150 mol) of LiAlH$_4$ in 150 mL of anhydrous diethylether cooled with ice bath is added a solution of the product obtained from step A in anhydrous diethylether, and the reaction mixture is stirred at the same temperature for 30 min. and at room temperature for 3 hours. The reaction is quenched with water saturated diethylether, then add 10% NaOH solution. After filtration, the filtrate is dried, and evaporated to give 9 g of crude product.

Step C: (1R,6R,9R)6,10,10-Trimethyl-11-oxatricyclo[7.2.1.0$^{1,6}$]dodec-2-ene

A mixture of compound obtained from step B, 200 mL of methanol, and 0.15 mL of hydrochloric acid is stirred at room temperature for 30 min. then neutralized with 3 N NaOH solution. After removal of methanol, the residue is purified by column chromatography to give 3.6 g of product in 45% yield calculated from step A.

Oil, $[\alpha]_D^{20}$+55.6° (C=1.5, acetone) MS: 206 (M$^+$, 39), 191 (100), 173 (20), 148 (47); $^1$H NMR (CDCl$_3$, δ): 0.94 (s, 3 H, 6-CH$_3$), 1.22 (s, 3 H, 10-CH$_3$), 1.34 (s, 3 H, 10-CH$_3$), 5.38 (d, J=10 Hz, 1 H, 2-H), 5.80 (m, 1 H, 3-H).

Preparation D (1S,2S,3S,6R,9R)6,10,10-Trimethyl-2,3-epoxy-11-oxatricyclo[7.2.1.06]dodecane

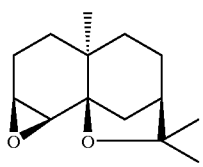

6.4 g (0.0204 mol) of m-chloroperbenzoic acid is add to a solution of 4 g (0.0194 mol)of (1R,6R,9R)6,10,10-trimethyl-11-oxatricyclo[7.2.1.0.1,6]dodec-2-ene in 80 mL of methylene chloride. The reaction mixture is stirred at room temperature for 5 days and filtered. The filtrate is washed with 10 mL of 1 N NaOH solution, dried, and evaporated. The residue is purified by column chromatography eluted with petroleum ether/ethyl acetate (10/1) to give 3.2 g white solid in 74% yield. mp 45–46° C., $[\alpha]_D^{20}$–40.7°, (C=1.4, acetone).

EXAMPLE 1

(1R,6S,9R)6,10,10-Trimethyl-2-propyl-11-oxatricyclo[7.2.1.0$^{1,6}$]dodec-2-ene

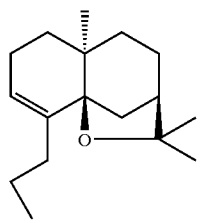

Step A: (6R/S,9R)6-Methyl-2-propyl-9-(1-methylvinyl)bicyclo[4.4.0]dec-1-ene-3-one

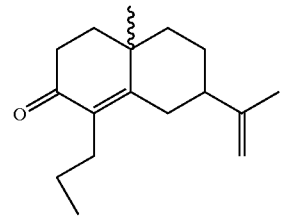

0.22 g(5.63 mmol) of potassium was dissolved in 8 mL of t-butanol under nitrogen by heating. To this solution was added the compound obtained from preparation A step C in t-butanol, then add a mixture of 0.69 g (3.75 mmol) of methyl iodide in 40 mL of t-butanol under reflux. After refluxing for 50 min. the reaction was cooled, neutralized with 10% HCl, and evaporated to dryness. The residue was taken up with 50 mL of ether, washed with brine, dried, and evaporated. The residue was purified by column chromatography eluted with petroleum ether/ethyl acetate (100/1) to give 0.592 g of product in 57% yield.

Step B: (6R/S,9R)6-Methyl-2-propyl-9-(1-methylepoxyethyl)bicyclo[4.4.0]dec-1-ene-3-one

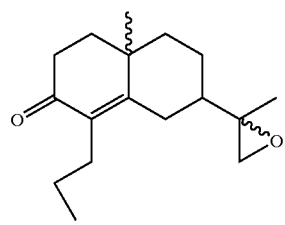

A mixture of 1.68 g (6.83 mmol) of compound obtained from step A, 1.24 g (7.17 mmol) of m-chloroperbenzoic acid was dissolved in 100 mL of methylene chloride and stirred at room temperature for 4 hours. After 4 filtration, the filtrate was washed with 10 mL of 1 N NaOH solution, brine, dried and evaporated to give title product.

Step C: (3R/S,6R/S,9R)6-Methyl-2-propyl-9-(1-hydroxy-isopropyl)-3-hydroxy-bicyclo[4.4.0]dec-1-ene

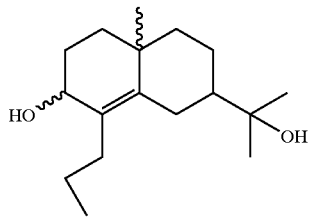

To a suspension of 0.69 g (18.3 mmol) of LiAlH$_4$ in 150 mL of anhydrous ether cooled with ice bath was added a solution of the compound obtained from step B in anhydrous ether. The reaction mixture was stirred for 30 min. with cooling, 3 hours at room temperature, then quenched with water saturated ether and 2 mL of 10% NaOH solution. After filtration, the solvent was removed by evaporation to give title product.

Step D: (1R,6S,9R)6,10,10-Trimethyl-2-propyl-11-oxatricyclo[7.2.1.0$^{1,6}$]dodec-2-ene A solution of 50 mL of concentrated HCl in 30 mL of methanol was added to the compound prepared in step C, and the reaction was stirred at room temperature for 30 min. After being neutralized with 3 N NaOH solution, the solvent was removed and the residue was purified by column chromatography eluted with petroleum ether/ethyl acetate (100/1) to give 0.525 g of product in 31% yield (three steps).

Oil, $[\alpha]_D^{17}$+17.4°, (C=0.73, ethanol); MS: 248 (M$^+$, 31), 57 (100); $^1$H NMR (CDCl$_3$, δ): 0.90 (m, 6 H, 6-CH$_3$, 3'-H), 1.24 (s, 3 H, 10-CH$_3$), 1.36 (s, 3 H, 10-CH$_3$), 5.56 (br. s, 1 H, 3-H).

EXAMPLE 2

(1R,6S,9R)6,10,10-Trimethyl-2-butyl-11-oxatricyclo[7.2.1.0$^{1,6}$]dodec-2-ene

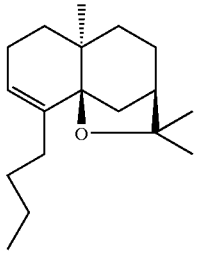

The compound was prepared according to the procedures in example 1, using butylbromide instead of propylbromide.

White solid, mp 24° C., $[\alpha]_D^{20}$=16.8°, (C=1.3, acetone); MS: 262 (M$^+$, 79), 244 (39), 219 (19), 147 (23), 41 (100); $^1$H NMR (CDCl$_3$, δ): 0.90 (s, 3 H, 6-CH$_3$), 1.23 (s, 3 H, 10-CH$_3$), 1.35 (s, 3 H, 10-CH$_3$), 5.73 (br.s, 1 H, 3-H).

EXAMPLE 3

(1R,6S,9R)6,10,10-Trimethyl-2-pentyl-11-oxatricyclo[7.2.1.0$^{1,6}$]dodec-2-ene

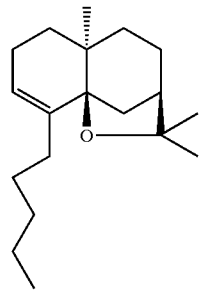

The compound was prepared according to the procedures in example 1, using pentylbromide instead of propylbromide.

Oil, $[C]_D^{17}$=19.2°, (C=0.53, acetone); MS: 277 (M+1), 276 (M$^+$, 100); $^1$H NMR (CDCl$_3$, δ): 0.92 (m, 6 H, 6-CH3+ 5'-H/2R), 1.26 (s, 3 H, 10-CH3), 1.38 (s, 3 H, 10-CH3), 5.56 (br.s, 1 H, 3-H).

EXAMPLE 4

(1R,6S,9R)6,10,10-Trimethyl-2-hexyl-11-oxatricyclo[7.2.1.0$^{1,6}$]dodec-2-ene

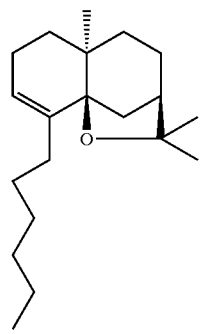

The compound was prepared according to the procedures in example 1, using hexylbromlde instead of propylbromide.

Oil; MS: 290 (M$^+$, 13), 275 (4), 219 (4), 123 (21), 105 (20), 81 (37), 55 (60), 41 (100); $^1$H NMR (CDCl$_3$, δ): 0.92 (s, 3 H, 6-CH$_3$), 1.26 (s, 3 H, 10-CH$_3$), 1.37 (s, 3 H, 10-CH$_3$), 5.56 (br.s, 1 H, 3-H).

EXAMPLE 5

(1R,6S,9R)6,10,10-Trimethyl-2-isopentyl-11-oxatricyclo[7.2.1.0$^{1,6}$]dodec-2-ene

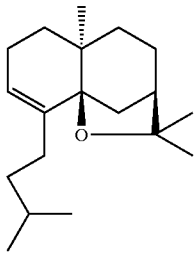

The compound was prepared according to the procedures in example 1, using 1-isopentylbromide instead of propylbromide.

White solid, mp 38–39° C. MS: 276 (M$^+$, 100), 261 (50), 258 (53), 243 (16), 220 (40), 123 (46), 91 (70), 55 (73). $^1$H NMR (CDCl$_3$, δ): 0.88 (s, 3 H, 3'-CH$_3$/2R), 0.92 (s, 3 H, 3'-CH$_3$/2R), 0.94 (s, 3 H, 6-CH$_3$), 1.25 (s, 3 H, 10-CH$_3$), 1.38 (s, 3 H, 10-CH$_3$), 5.56 (s, 1 H, 3-H).

EXAMPLE 6

(1R,6S,9R)6,10,10-Trimethyl-2-decyl-11-oxatricyclo[7.2.1.0$^{1,6}$]dodec-2-ene

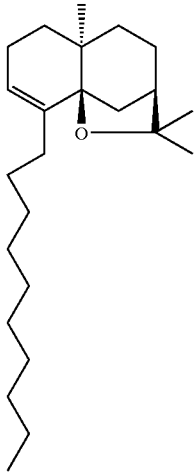

The compound was prepared according to the procedures in example 1, using decyl bromide instead of propylbromide.

MS: 346 (M+, 5), 328 (100), 313 (22), 202 (25), 187 (58), 131 (41), 81 (21), 55 (32), 41 (62); $^1$H NMR (CDCl$_3$, δ): 0.94 (s, 3 H, 6-CH$_3$), 1.28 (s, 3 H, 10-CH$_3$), 1.38 (s, 3 H, 10-CH$_3$), 5.58 (br.s, 1 H, 3-H).

EXAMPLE 7

(1R,6S,9R)6,10,10-Trimethyl-2-benzyl-11-oxatricyclo[7.2.1.0$^{1,6}$]dodec-2-ene

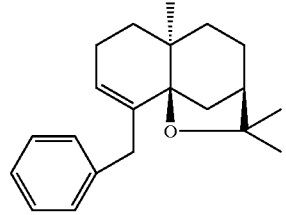

The compound was prepared according to the procedures described in example 1, using benzyl bromide instead of propylbromide.

White solid, mp 49–50° C. MS: 279 (M+1, 22), 296 (M+, 100), 278 (43), 200 (11), 158 (32), 91 (88); $^1$H NMR (CDCl$_3$, δ): 0.98 (s, 3 H, 6-CH$_3$), 1.30 (s, 3 H, 10-CH$_3$), 1.40 (s, 3 H, 10-CH$_3$), 3.44 (s, 2 H, CH$_2$Ph), 5.54 (br.s, 1 H, 3-H), 7.22 (s, 5 H, Ph-H).

EXAMPLE 8

(1R,6S,9R)6,10,10-Trimethyl-2-(4-flurobenzyl)-11-oxatricyclo[7.2.1.0$^{1,6}$]dodec-2-ene

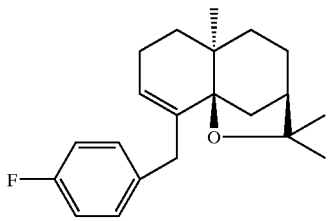

The compound was prepared according to the procedures described in example 1, using 4-flurobenzyl bromide instead of propylbromide.

White solid, mp 131–133° C., MS: 314 (M$^+$, 30), 296 (28), 176 (26), 147 (20), 123 (17), 109 (100); $^1$H NMR (CDCl$_3$, δ): 0.96 (s, 3 H, 6-CH$_3$), 1.28 (s, 3 H, 10-CH$_3$), 1.40 (s, 3 H, 10-CH$_3$), 3.79 (s, 2 H, CH$_2$Ar), 5.50 (br.s, 1 H, 3-H), 7.22–6.84 (m, 4 H, Ph-H).

EXAMPLE 9

(1R,6S,9R)6,10,10-Trimethyl-2-(4-methoxybenzyl)-11-oxatricyclo[7.2.1.0$^{1,6}$]-2-ene

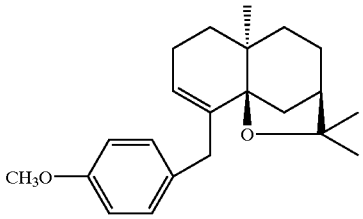

The compound was prepared according to the procedures described in example 1, using 4-methoxybenzyl bromide instead of propylbromide.

White solid. MS: 327 (M+1, 22), 326 (M⁺, 60), 308 (43), 121 (100); ¹H NMR (CDCl₃, δ): 0.96 (s, 3 H, 6-CH₃), 1.28 (s, 3 H, 10-CH₃), 1.40 (s, 3 H, 10-CH₃), 3.36 (s, 2 H, C$\underline{H}_2$Ar), 3.80 (s, 3 H, OCH₃), 5.50 (br.s, 1 H, 3-H), 6.80 (d, J=8.5 Hz, 2 H, Ar—H), 7.10 (d, J=8.5 Hz, 2 H, Ar—H).

EXAMPLE 10

(1R,6S,9R)6,10,10-Trimethyl-2-(4-chlorobenzyl)-11-oxatricyclo[7.2.1.0$^{1,6}$]dodec-2-ene

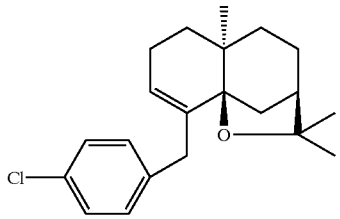

The compound was prepared according to the procedures described in example 1, using 4-chlorobenzyl bromide instead of propylbromide.

White solid, mp 87–88 MS: 332 (M⁺, 14), 330 (40), 312 (28), 277 (13), 192 (22), 147 (21), 125 (100); ¹H NMR (CDCl₃, δ): 0.92 (s, 3 H, 6-CH₃), 1.24 (s, 3 H, 10-CH₃), 1.37 (s, 3 H, 10-CH₃), 3.36 (s, 2 H, C$\underline{H}_2$Ar), 5.48 (br.s, 1 H, 3-H), 7.03–7.26 (m, 4 H, Ar—H).

EXAMPLE 11

(1R,6S,9R)6,10,10-Trimethyl-2-(2-hydroxyethyl)-11-oxatricyclo[7.2.1.0$^{1,6}$]dodec-2-ene

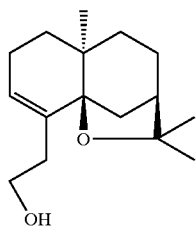

Step A: Ethyl(6R/S,9R)6-Methyl-9-(1-methylvinyl)bicyclo[4.4.0]dec-1-ene-3-one-2-acetate

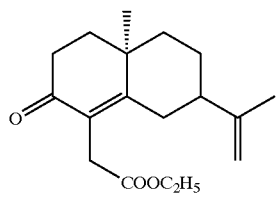

1 g (25.6 mmol) of potassium was dissolved in 25 mL of t-butanol under protection of nitrogen, then 15 mL of t-butanol was distilled out. To this remaining solution was added a solution of the compound obtained from preparation A step C in 40 mL of anhydrous benzene and part of the benzene was distilled out to keep about 30–40 mL of reaction solution. After being cooled to room temperature, 5 g (32.7 mmol) of ethyl bromoacetate was added and the mixture was stirred for 7 hours, then diluted with 100 ml of ether, washed with brine, dried and evaporated. The residue was purified by column chromatography (petroleum ether/ethyl acetate 10/1, 8/1, 5/1)to give 1.9 g of product in 45% yield.

Step B: Ethyl(6R/S,9R)6-Methyl-9-(1-methyl-epoxyethyl)bicyclo[4.4.0]dec-1-ene-3-one-2-acetate

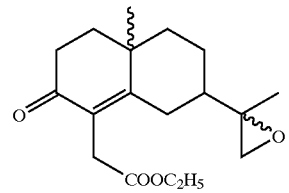

The compound was prepared according to the procedures described Step B in example 1, from the compound prepared in the above step A.

Step C: (3R/S,6R/S,9R)6-Methyl-3-hydroxy-2-(2-hydroxyethyl)-9-(1-hydroxyisopropyl)bicyclo[4.4.0]dec-1-ene

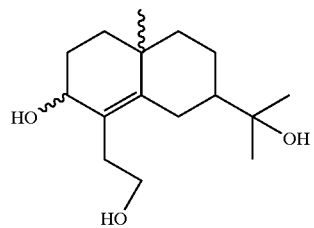

The compound was prepared according to the procedures described Step C in example 1, from the compound prepared in the above step B.

Step D: (1R,6S,9R)6,10,10-Trimethyl-2-(2-hydroxyethyl)-1-oxatricyclo[7.2.1.0$^{1,6}$]dodec-2-ene The compound was prepared according to the procedures described Step D in example 1, from the compound prepared in the above step C to give 0.5 g of product in 31% yield (three steps).

White solid, mp 34–36° C., [α]$_D$$^{17}$+31.6° (c=0.75, ethanol) MS: 250 (M⁺, 24), 136 (100). ¹H NMR (CDCl₃, δ): 0.94 (s, 3 H, 6-CH₃), 1.28 (s, 3 H, 10-CH₃), 1.39 (s, 3 H, 10-CH₃), 3.6–3.8 (m, 2 H, 2'-H/2R), 5.70 (t, J=3.6 Hz, 1 H, 3-H).

EXAMPLE 12

(1R,6S,9R)6,10,10-Trimethyl-2-(3-hydroxypropyl)-11-oxatricyclo[7.2.1.0$^{1,6}$]dodec-2-ene

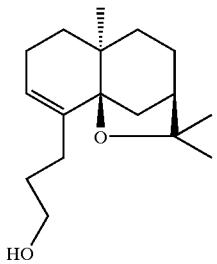

The compound was prepared according to the procedure described step A in example 1 using 3-bromopropyl tetrahydropyranyl ether obtained from step B of preparation B instead of propylbromide.

Oil, [α]$_D$$^{10}$+24.6°, (c=0.62, chloroform) MS: 264 (M⁺, 85), 249 (7), 246 (15), 231 (8), 41 (100). ¹H NMR (CDCl₃, δ): 0.89 (s, 3 H, 6-CH₃), 1.23 (s, 3 H, 10-CH₃), 1.34 (s, 3 H, 10-CH₃), 3.64 (t, J=7.0 Hz, 2 H, 3'-H/2R), 5.70 (t, J=3.6 Hz, 1 H, 3-H).

EXAMPLE 13

(1R,6S,9R)6,10,10-Trimethyl-2-[2-(N,N-diethyamino-)ethyl]-11-oxatricyclo[7.2.1.0^{1,6}]dodec-2-ene

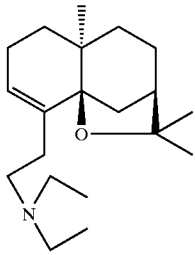

Step A: (1R,6S,9R)6,10,10-Trimethyl-2-(2-p-toluenesufornyl)ethyl-11-oxa-tricyclo[7.2.1.0^{1,6}]dodec-2-ene

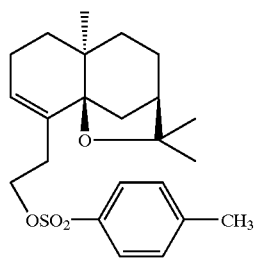

300 mg (1.2 mmol) of the compound obtained from step D of example 11 step D and 300 mg (1.57 mmol) of p-toluenesulfonyl chloride was dissolved in 3 mL of pyridine and allowed to stand for 12 hours in ice bath. 50 mL of ether was added and the solution was washed with copper sulfate and brine, dried, and evaporated. The residue was purified by column chromatography of silica gel to give 390 mg of product as white solid. yield 80%. mp 108–109°C.

Step B: (1R,6S,9R)6,10,10-Trimethyl-2-[2-(N,N-diethyamino-)ethyl]-11-oxatricyclo[7.2.1.0^{1,6}]dodec-2-ene 150 mg (0.97 mmol) of the compound obtained from the step A was added to 2 mL of diethylamine and stirred at 80° C. for 1.5 hours. Then 50 mL of ether was added and washed successively with water, 10% NaOH solution and brine, dried and evaporated to dryness. The residue was purified by column chromatography of silica gel (petroleum ether/ethyl acetate/methanol 10/5/1) to give 110 mg of product, yield 97%.

Oil, $[\alpha]_D^{20}$+32.6° (c=0.34, chloroform); MS: 306 (M+1, 23), 290 (6), 86 (100); $^1$H NMR (CDCl$_3$, δ): 0.91 (s, 3 H, 6-CH$_3$), 1.06 (t, J=7.1 Hz, 9 H, NCH$_2$CH$_3$), 1.26 (s, 3 H, 10-CH$_3$), 1.37 (s, 3 H, 10-CH$_3$), 2.58 (m, 6 H, NCH$_2$CH$_3$), 5.61 (br.s, 1 H, 3-H).

EXAMPLE 14

(1R,6S,9R)6,10,10-Trimethyl-2-[2-(N-cyclohexylamino-)ethyl]-11-oxatricyclo[7.2.1.0^{1,6}]dodec-2-ene

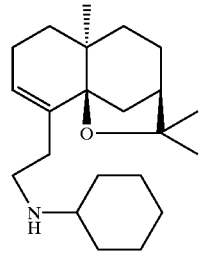

The compound was prepared according to the procedures described step B in example 13, using cyclohexyl amine instead of diethyl amine.

Oil, $[\alpha]_D^{20}$+71.7° (c=0.12, chloroform); MS: 331 (M+, 3), 302 (2), 279 (2), 278 (2), 258 (5), 167 (7), 149 (30), 98 (100); $^1$H NMR (CDCl$_3$, δ): 0.90 (s, 3 H, 6-CH$_3$), 1.23 (s, 3 H, 10-CH$_3$), 1.36 (s, 3 H, 10-CH$_3$), 5.61 (br.s, 1 H, 3-H).

EXAMPLE 15

(1R,6S,9R)6,10,10-Trimethyl-2-[2-(1-imidazole)ethyl]-11-oxatricyclo[7.2.1.0^{1,6}]dodec-2-ene

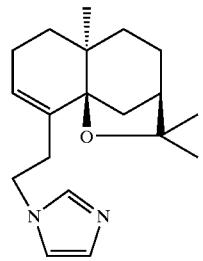

A solution of 150 mg (0.97 mmol) of the compound obtained from step A of example 13 step A and 150 mg (2.2 mmol) of imidazole in 5 mL of methanol was put in a sealed tube to react at 80° C. for 1.5 hours. After removal of solvent, the residue was purified by column chromatography of silica gel (petroleum ether/ethyl acetate/methanol 10/5/1) to give 70 mg of product in 63% yield.

Oil, $[\alpha]_D^{10}$+33.4° (c 0.63, chloroform); MS: 301 (M+1, 100), 286 (35), 242 (60); $^1$H NMR (CDCl$_3$, δ): 0.91 (s, 3 H, 6-CH$_3$), 1.23 (s, 3 H, 10-CH$_3$), 1.37 (s, 3 H, 10-CH$_3$), 2.48 (br.t, J=7.7 Hz, 2 H, 1'-H/2R), 4.03 (m, 2 H, 2'-H/2R), 5.50 (t, J=3.6 Hz, 1 H, 3-H), 6.92 (s, 1 H, 5"-H/2R), 7.05 (s, 1 H, 4"-H/2R), 7.52 (s, 1 H, 2"-H/2R).

EXAMPLE 16

(1R,2S,6S,9R)6,10,10-Trimethyl-2-butyl-2-hydroxy-11-oxatricyclo[7.2.1.0$^{1,6}$]dodecane

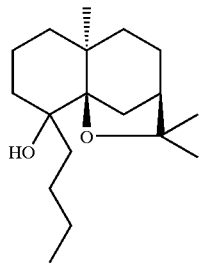

Step A: (1R,2S,6S,9R)6,10,10-Trimethyl-2-butyl-2,3-epoxy-11-oxatricyclo[7.2.1.0$^{1,6}$]dodecane

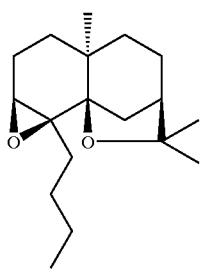

A mixture of 262 mg (1 mmol) of the compound obtained from step D of example 2 and 330 mg (1.05 mmol) of m-chloroperbenzoic acid in 10 mL of methylene chloride was stirred at room temperature for 4 hours, then washed with 1 N NaOH solution and brine, dried and evaporated to give 272 mg of product as white crystals, mp 70–72° C., $[\alpha]_D^{10}$ –27.4° (c=0.95, ethanol).

MS: 278 (M+, 3), 263 (20), 235 (2), 221 (5), 193 (4), 167 (20), 41 (100); $^1$H NMR (CDCl$_3$, δ): 0.83 (s, 3 H, 6-CH$_3$), 0.87 (t, J=7.4 Hz, 3 H, 4'-CH$_3$) 1.28 (s, 3 H, 10-CH$_3$), 1.35 (s, 3 H, 10-CH$_3$), 2.94 (br.s, 1 H, 3-H).

Step B: (1R,2S,6S,9R)6,10,10-Trimethyl-2-butyl-2-hydroxy-11-oxatricyclo[7.2.1.0$^{1,6}$]dodecane To a suspension of 180 mg (1.39 mmol) of AlCl3 in 15 mL of ether cooled with ice bath was added 154 mg (4.05 mmol) of LiAlH$_4$ and the mixture was stirred for 5 min. then at room temperature for 30 min. Then, a solution of 270 mg (0.97 mmol) of the compound obtained from the step A in 10 mL of ether was added, stirred for 2 hours, and quenched with water saturated ether and 10 mL of 10% HCl. The organic layer was dried and evaporated to dryness and the residue was purified by column chromatography (silica gel, petroleum ether/ethyl acetate 30/1) to give 230 mg of product, yield 85%.

$[\alpha]_D^{17}$ –57.4° (c=1.7, ethanol). MS: 280 (M$^+$, 3), 263 (2), 219 (2), 205 (2) 198 (20), 98 (20), 43 (100); $^1$H NMR (CDCl$_3$, δ): 0.90 (s, 3 H, 3'-CH$_3$/2R), 1.04 (s, 3 H, 6-CH$_3$), 1.16 (s, 3 H, 10-CH$_3$), 1.29 (s, 3 H, 10-CH$_3$), 2.50 (br.s, 1 H, 2-OH).

EXAMPLE 17

(1R,6S,9R)6,10,10-Trimethyl-2-butylene-11-oxatricyclo[7.2.1.0$^{1,6}$]dodecane

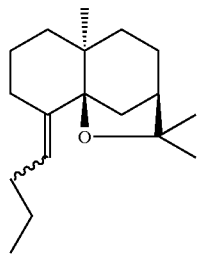

To a solution of 120 mg (0.429 mmol) of the compound prepared from step B in example 16 step B in 1.5 mL of pyridine was added 0.4 mL of thionyl chloride dropwise, and the reaction was stirred for 2 hours. After workup, the crude product was purified by column chromatography to give 80 mg of title product, 71% yield.

Oil, $[\alpha]_D^{17}$ –165.8° (c=0.44, ethanol). MS: 263 (M+1, 19), 262 (M$^+$, 52), 201 (100); $^1$H NMR (CDCl$_3$, δ): 0.96 (s, 3 H, 6-CH$_3$), 1.15 (s, 3 H, 10-CH$_3$), 1.37 (s, 3 H, 10-CH$_3$), 5.12 (t, J=7.2 Hz, 1'-H).

EXAMPLE 18

(1S,2R,6S,9R)6,10,10-Trimethyl-2-butyl-11-oxatricyclo[7.2.1.0$^{1,6}$]dodecane

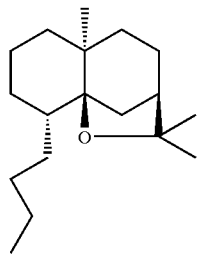

To a solution of 50 mg (0.19 mmol) of the compound obtained from example 17 in 1 mL of anhydrous ether was added 10 mg of PtO$_2$, and the mixture was stirred under hydrogen at 35° C. for 7 hours. After filtration, the solvent was removed and the residue was purified by column chromatography of silica gel to give 48 mg of title product, yield 95%.

Oil, $[\alpha]_D^{17}$ –26° (c=0.46, chloroform). MS: 264 (M$^+$, 60), 249 (100), 220 (60), 193 (35), 179 (60); $^1$H NMR (CDCl$_3$, δ): 0.89 (t, J=7.3 Hz, 3 H, 3'-CH3/2R), 0.99 (s, 3 H, 6-CH$_3$), 1.15 (s, 3 H, 10-CH$_3$), 1.36 (s, 3 H, 10-CH$_3$).

EXAMPLE 19

(1S,2S,6S,9R)6,10,10-Trimethyl-2-(3-hydroxypropyl)-11-oxatricyclo[7.2.1.0$^{1,6}$]dodecane

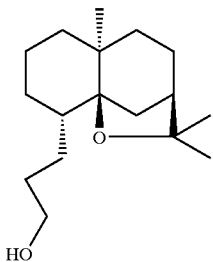

and (1S,2R,6S,9R)6,10,10-Trimethyl-2-(3-hydroxypropyl)-11-oxatricyclo[7.2.1.0$^{1,6}$]dodecane

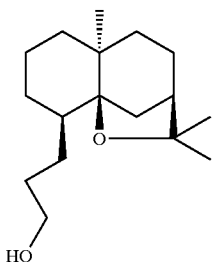

50 mg (0.189 mmol) of the compound prepared from step D in example 12 was dissolved in 1.5 mL of glacial acetic acid and hydrogenated over 50 mg of 5% Rh/C for 8 hours. After filtration and removal of acetic acid, the residue was purified by column chromatography (silica gel, petroleum ether/ethyl acetate 15/1) to give product.

(1S,2S,6S,9R)6,10,10-Trimethyl-2-(3-hydroxypropyl)-11-oxatricyclo[7.2.1.0$^{1,6}$]dodecane:

Oil, 2 mg, yield 4%, $[\alpha]_D^{10}$ −25.4° (c=0.26, chloroform). MS: 266 (M$^+$, 50), 25 (100), 233 (30), 149 (50); $^1$H NMR (CDCl$_3$, δ): 0.99 (s, 3 H, 6-CH$_3$), 1.15 (s, 3 H, 10-CH$_3$), 1.36 (s, 3 H, 10-CH$_3$) 3.64 (t, J=6.6 Hz, 2 H, 3'-H/2R).

(1S,2R,6S,9R)6,10,10-Trimethyl-2-(3-hydroxypropyl)-11-oxatricyclo[7.2.1.0$^{1,6}$]dodecane Oil, 5 mg, yield 10%, $[\alpha]_D^{10}$ −95.3° (c=0.22, chloroform). MS: 266 (M$^+$, 38), 25 (100), 233 (30), 149 (58); $^1$H NMR (CDCl$_3$, δ): 1.02 (s, 3 H, 6-CH$_3$), 1.16 (s, 3 H, 10-CH$_3$), 1.36 (s, 3 H, 10-CH$_3$) 3.65 (t, J=7.8 Hz, 2 H, 3'-H/2R).

EXAMPLE 20

(1S,2S,6S,9R)6,10,10-Trimethyl-2-butyl-11-oxatricyclo[7.2.1.0$^{1,6}$]dodecane

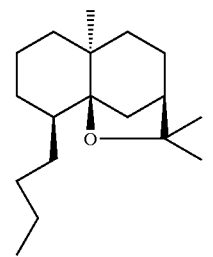

Step A: (1S,2S,6S,9R)6,10,10-Trimethyl-2-(3-p-toluenesulfonyloxy)propyl-11-oxatricyclo[7.2.1.0$^{1,6}$]dodecane

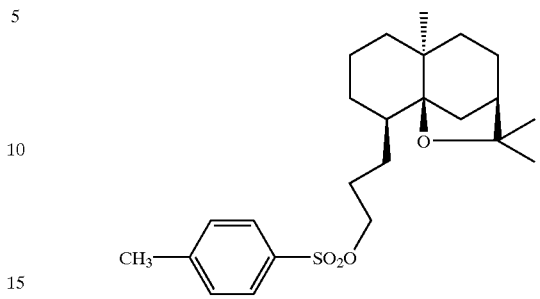

To a solution of 10 mg (0.037 mmol) of (1S,2S,6S,9R) 6,10,10-trimethyl-2-(3-hydroxypropyl)-11-oxatricyclo [7.2.1.0$^{1,6}$]dodecane obtained from example 19 in 1 mL of pyridine was added 10 mg (0.0628 mmol) of p-toluenesulfonyl chloride and allowed to stand at 5° C. for 12 hours. To the reaction mixture was added 0.1 mL of water, allowed to stand for one more hour, then added 20 mL of ether; washed with 3 N HCl, 10% NaOH solution and brine, dried and evaporated to give 10 mg of crude product.

Step B: (1S,2S,6S,9R)6,10,10-Trimethyl-2-butyl-11-oxatricyclo[7.2.1.0$^{1,6}$]dodecane 10 mg of the compound prepared in the above step A was added to the Grignard reagent prepared from 50 mg (2.08 mmol) of magnesium and 285 mg (2.01 mmol) of methyliodide. The reaction mixture was stirred at room temperature for 3 hours, then quenched with saturated ammonium chloride solution. The ether layer was washed with brine, dried and evaporated and the residue was purified by thin layer chromatography (silica gel, cyclohexane/ether 80/1, three times developing) to give 2 mg of title product, yield 10%.

MS: 264 (M$^+$, 17), 249 (42), 221 (45), 193 (22), 179 (50), 167 (23), 149 (32), 55 (100); $^1$H NMR (CDCl$_3$, δ): 0.89 (t, J=7.1 Hz, 3 H, 4'-H/2R) 1.02 (s, 3 H, 6-CH$_3$), 1.15 (s, 3 H, 10-CH$_3$), 1.33 (s, 3 H, 10-CH$_3$).

EXAMPLE 21

(1R,2R,6S,9R)6,10,10-Trimethyl-2-butyl-2-hydroxy-11-oxatricyclo[7.2.1.0$^{1,6}$]dodecane

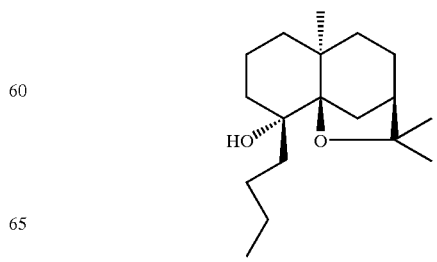

Step A: (1S,2S,3S,6S,9R)6,10,10-Trimethyl-2,3-epoxy-11-oxatricyclo[7.2.1.0¹,⁶]dodecane

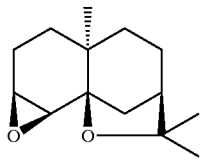

The compound was prepared following the published procedures (J. W. Huffman and R. C. Desai, J. Org. Chem., 47, 3254, 1982).

Step B: (1S,2S,6S,9R)6,10,10-Trimethyl-2-hydroxy-11-oxatricyclo[7.2.1.0¹,⁶]dodecanol

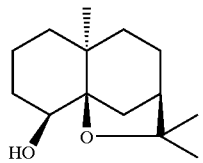

and (1S,3S,6S,9R)6,10,10-Trimethyl-3-hydroxy-11-oxatricyclo[7.2.1.0¹,⁶]dodecanol

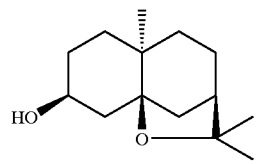

950 mg (25 mmol) of LiAlH$_4$ was added into the suspension of 4 g (31 mmol) of AlCl$_3$ in 80 mL of ether under nitrogen in ice bath. After 5 min. the temperature was raised to room temperature and stirred for 30 min. then cooled again with ice bath. A solution of 2 g (9 mmol) of the compound prepared in the preparation D in 10 mL of ether was added to the reaction mixture and stirred for 1 hour and 20 min. After workup, (1S,2S,6S,9R)6,10,10-trimethyl-2-hydroxy-11-oxatricyclo[7.2.1.0¹,⁶]dodecane and (1S,3S,6S,9R)6,10,10-trimethyl-3-hydroxy-11-oxatricyclo[7.2.1.0¹,⁶]dodecane were obtained as a mixture.

Step C: (1R,6S,9R)6,10,10-Trimethyl-11-oxatricyclo[7.2.1.0¹,⁶]dodecan-2-one

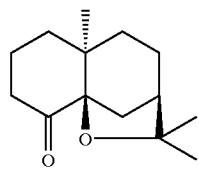

and (1S,6R,9R)6,10,10-Trimethyl-11-oxatricyclo[7.2.1.0¹,⁶]dodecan-3-one

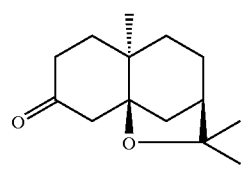

To a mixture of the compounds obtained from the step B in 5 mL of methylene chloride was added 1.6 g (7.44 mmol) of pyridinium chlorochromate (PCC) (700 mg the first time, and the rest of the 900 mg in three times at 10 hour intervals), stirred for 6 hours, then 30 mL of ether was added. After 10 min. of stirring, the reaction mixture was filtered through celite and the filtrate was washed with brine, dried and evaporated. The residue was purified by column chromatography (silica gel, petroleum ether/ethyl acetate 20/1 and 4/1) to give 233 mg of (1R,6S,9R)6,10,10-trimethyl-11-oxatricyclo[7.2.1.0¹,⁶]dodecan-2-one as white solid, yield 59%, Mp 55–56° C., [α]$_D^{10}$–123.8° (c=1.15, chloroform); 70 mg of (1S,6R,9R)6,10,10-trimethyl-11-oxatricyclo[7.2.1.0¹,⁶]dodecan-3-one, yield 18%, mp 60–61° C., [α]$_D^{17}$–22.9° (c=0.55, ethanol).

Step D: (1R,2R,6S,9R)6,10,10-Trimethyl-2-butyl-2-hydroxy-11-oxatricyclo[7.2.1.0¹,⁶]dodecane To a solution of 400 mg (1.82 mmol) of (1R,6S,9R)6,10,10-trimethyl-11-oxatricyclo[7.2.1016]dodecan-2-one obtained from step C in 3 mL anhydrous ether in ice bath was added butyl lithium solution (2 mL, 1.6 M in cyclohexane) under nitrogen, and stirred for 30 min. After work-up, the crude product was purified by column chromatography (silica gel, petroleum ether/ethyl acetate 4/1) to give 420 mg of title product, yield 83%.

White solid, mp 90–92° C., [α]$_D^{10}$–66.8° (c=0.66, chloroform) MS: 280 (M⁺, 100), 265 (20), 247 (10), 198 (60), 162 (50); ¹H NMR (CDCl$_3$, δ): 0.89. (t, J=7.0 Hz, 3 H, 3'-CH3/2R), 1.15 (s, 3 H, 6-CH$_3$), 1.26 (s, 3 H, 10-CH$_3$), 1.33 (s, 3 H, 10-CH$_3$).

EXAMPLE 22

(1S,2S,3S,6R,9R)6,10,10-Trimethyl-2-butyl-3-hydroxy-11-oxatricyclo[7.2.1.0¹,⁶]dodecane

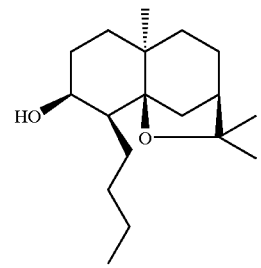

A solution of 400 mg (1.44 mmol) of the compound prepared in step A of example 10 step A in 5 mL of tetrahydrofuran was added dropwise to a refluxing solution of 262 mg (6.9 mmol) of LiAlH$_4$ in 12 ml of tetrahydrofuran and stirred for 3 hours. After work up, the crude product was purified by column chromatography (silica gel, petroleum ether/ethyl acetate 40/1) to give 140 mg of title product, yield 35%.

White solid, mp 47–48° C., [α]$_D^{17}$–22.7° (c=0.44, chloroform) MS: 280 (M⁺, 40), 265 (30), 247 (40), 204 (90), 195 (75), 167 (60), 41 (100); ¹H NMR (CDCl$_3$, δ): 0.89 (t, J=7.0 Hz, 3 H, 3'-CH3/2R), 0.98 (s, 3 H, 6-CH$_3$), 1.16 (s, 3 H, 10-CH$_3$), 1.32 (s, 3 H, 10-CH$_3$), 3.81 (br.d, J=3.7 Hz, 1 H, 3-OH).

EXAMPLE 23

(1S,2R,6R,9R)6,10,10-Trimethyl-2-butyl-11-oxatricyclo[7.2.1.0$^{1,6}$]dodecan-3-one

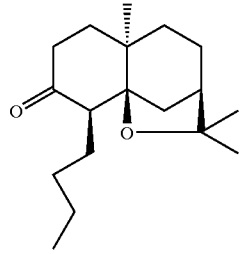

To a solution of 130 mg (0.46 mmol) of the compound prepared in example 22 in 2 mL of methylene chloride was added 100 mg (0.46 mmol) of PCC, and the reaction mixture was stirred for 5 hours at room temperature. Another 64 mg (0.30 mmol) of PCC in two batches was added to the reaction at an interval of 5 hours, and stirred for 5 hours. After work-up, the crude product was purified by column chromatography (silica gel, petroleum ether/ethyl acetate 40/1) to give 115 mg of title product, yield 90%.

White solid, mp 64–66° C., $[\alpha]_D^{17}$–10.3° (c=0.58, chloroform). MS: 278 (M$^+$, 85), 263 (55), 235 (75), 164 (100); $^1$H NMR (CDCl$_3$, δ): 0.92 (t, J=7.0 Hz, 3 H, 3'-CH$_3$/2R), 1.19 (s, 3 H, 6-CH$_3$), 1.29 (s, 3 H, 10-CH$_3$), 1.32 (s, 3 H, 10-CH$_3$).

EXAMPLE 24

(1S,3S,6R,9R)3,6,10,10-Tetramethyl-3-hydoxy-11-oxatricyclo[7.2.1.0$^{1,6}$]dodecane

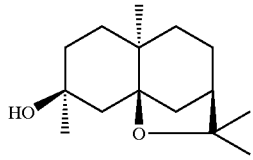

The Grignard reagent prepared from 120 mg (5 mmol) of magnesium and 710 mg (5 mmol) of methyl iodide in 10 mL of ether was added dropwise to a solution of 300 mg (1.35 mmol) of (1S,6R,9R)6,10,10-trimethyl-11-oxatricyclo[7.2.1.0$^{1,6}$]dodecan-3-one prepared from step C in example 21 in 5 mL of ether cooled with ice-salt mixture. The reaction mixture was stirred at 15° C. for 1 hour then worked up. The crude product was purified by column chromatography (silica gel, petroleum ether/ethyl acetate 40/1) to give 200 mg of product, yield 62%.

White crystals, mp 68–70° C., $[\alpha]_D^{17}$–62.2° (c=1.8, ethanol). MS: 239 (M+1, 11), 23 8 (M$^+$, 46), 153 (100); $^1$H NMR (CDCl$_3$, δ): 0.96 (s, 3 H, 6-CH$_3$), 1.16 (s, 3 H, 10-CH$_3$), 1.20 (s, 3 H, 3-CH$_3$), 1.35 (s, 3 H, 10-CH$_3$).

EXAMPLE 25

(1S,3S,6R,9R)6,10,10-Trimethyl-3-butyl-3-hydroxy-11-oxatricyclo[7.2.1.0$^{1,6}$]dodecane

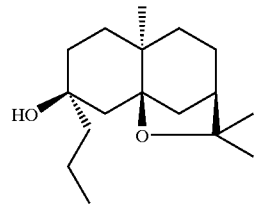

The compound was prepared according to the procedures described in example 24, using butyl bromide instead of methyl iodide.

Solid, mp 25–26° C., $[\alpha]_D^{17}$–30.8° (c=0.61, ethanol). MS: 280 (M+, 39), 205 (23), 195 (100); $^1$H NMR (CDCl$_3$, δ): 0.96 (t, J=7.0 Hz, 3 H, 3'-CH3/3R), 1.20 (s, 3 H, 6-CH$_3$), 1.35 (s, 3 H, 10-CH$_3$), 1.36 (s, 3 H, 10-CH$_3$).

EXAMPLE 26

(1S,3R,6R,9R)6,10,10-Trimethyl-3-bromo-11-oxatricyclo[7.2.1.0$^{1,6}$]dodecane

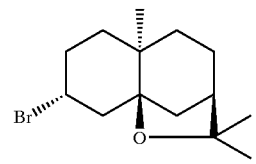

Step A: (1S,3S,6R,9R)6,10,10-Trimethyl-3-hydroxy-11-oxatricyclo[7.2.1.0$^{1,6}$]dodecane

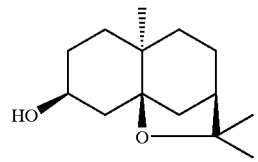

Method 1: the compound was prepared according to the procedures described as step A, in example 15.

Method 2: 1.1 g (5 mmol) of the compound from preparation D in 10 mL of anhydrous ether was added to a suspension of 475 mg (12.5 mmol) of LiAlH4 in 50 mL of anhydrous ether, and the reaction was stirred for 2 hours at room temperature. After work-up, the crude product was purified by column chromatography (silica gel, petroleum ether/ethyl acetate 8/1) to give 0.9 g of title product, yield 81%

White solid, mp 58–59° C., $[\alpha]_D^{17}$–37.7° (c=0.73, ethanol).

Step B: (1S,3R,6R,9R)6,10,10-Trimethyl-3-bromo-11-oxatricyclo[7.2.1.0$^{1,6}$]dodecane A mixture of 500 mg (1.84 mmol) of phosphorus tribromide, 10 mL of anhydrous ether, and 370 mg (1.41 mmol) of triphenyl phosphine was added to 150 mg (0.67 mmol) of the compound from the step A cooled with ice bath, and the reaction mixture was stirred for 2 hours. 5 mL of water and 20 mL of ether was added, the ether layer was washed with saturated NaHCO$_3$ solution, and brine, dried and evaporated. The crude product was purified by column chromatography (silica gel, petroleum ether/ethyl acetate 80/1) to give 87 mg of title product, yield 36%.

Oil, $[\alpha]_D^{17}$ −54.6° (c=0.87, chloroform). MS: 287 (M+, 4), 285 (M+, 4), 273 (100); $^1$H NMR (CDCl$_3$, δ): 1.04 (s, 3 H, 6-CH$_3$), 1.16 (s, 3 H, 10-CH$_3$), 1.32 (s, 3 H, 10-CH$_3$), 3.34 (tt, J=12.3, 6.4 Hz, 1 H, 3-H).

EXAMPLE 27

(1R,1'R,6S,9R)6,10,10-Trimethyl-2-(1-hydroxybutyl)-11-oxatricyclo[7.2.1.0$^{1,6}$]dodec-2-ene

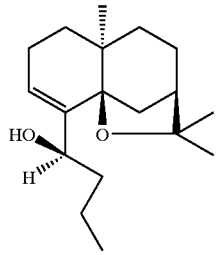

and (1R,1'S,6S,9R)6,10,10-Trimethyl-2-(1-hydroxybutyl)-11-oxatricyclo[7.2.1.0$^{1,6}$]dodec-2-ene

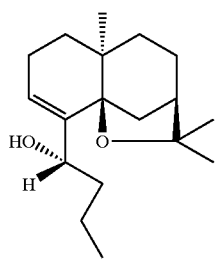

Step A: (1R,6S,9R)6,10,10-Trimethyl-2-hydoxymethyl-11-oxatricyclo[7.2.1.0$^{1,6}$]dodec-2-ene

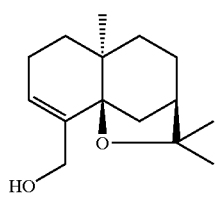

The compound was prepared according to the procedures described in Chinese Chem. Lett. 1991, 2(6), 425–428.

Step B: (1R,6S,9R)6,10,10-Trimethyl-2-carbonyl-11-oxatricyclo[7.2.1.0$^{1,6}$]dodec-2-ene

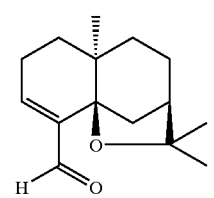

To a solution of 150 mg (0.636 mmol) of the compound obtained from the step A in 2 mL of methylene chloride was added 250 mg (1.16 mmol) of PCC, and the reaction was stirred at room temperature for 2 hours, then 50 mg (0.23 mmol) of PCC was added. After being stirred for 1 hour, 20 mL of ether was added, and filtered. The ether layer was washed with brine, dried and evaporated. The residue was purified by column chromatography (silica gel, petroleum ether/ethyl acetate 5/1) to give 120 mg of product, yield 81%.

Step C: (1R,1'R,6S,9R)6,10,10-Trimethyl-2-(1-hydroxybutyl)-11-oxatricyclo[7.2.1.0$^{1,6}$]dodec-2-ene and (1R,1'S,6S,9R)6,10,10-Trimethyl-2-(1-hydroxybutyl)-11-oxatricyclo[7.2.1.0$^{1,6}$]dodec-2-ene A solution of 100 mg (0.427 mmol) of (1R,6S,9R)6,10,10-oxatrimethyl-2-carbonyl-1-oxatricyclo[7.2.1.01,6]dodec-2-ene from step B in 5 mL of ether was added dropwise to the Grignard reagent prepared from 246 mg (2 mmol) of propyl bromide and 60 mg (2.5 mmol) of magnesium in ether under nitrogen. After being stirred for 10 min, the reaction was quenched by addition of saturated ammonium chloride solution, then washed with brine, dried, and evaporated. The residue was purified by column chromatography to give (1R,1'R,6S,9R)6,10,10-trimethyl-2-(1-hydroxybutyl)-11-tricyclo[7.2.1.0$^{1,6}$]dodec-2-ene 18 mg and (1R,1'S,6S,9R)6,10,10-trimethyl-2-(1-hydroxybutyl)-11-tricyclo[7.2.1.0$^{1,6}$]dodec-2-ene 72 mg, yield 15% and 61% respectively.

(1R,1'R,6S,9R)6,10,10-trimethyl-2-(1-hydroxybutyl)-11-oxatricyclo[7.2.1.0$^{1,6}$]dodec-2-ene: Oil, $[\alpha]_D^{10}$ −176.7° (c=0.1, chloroform).

MS: 279 (M+1, 10), 243 (79), 236 (62), 228 (45), 218 (82), 200 (95), 157 (100); $^1$H NMR (CDCl$_3$, δ): 0.90 (s, 3 H, 6-CH$_3$), 0.94 (t, J=7.2 Hz, 3 H, 3'-CH$_3$/2R), 1.28 (s, 3 H, 10-CH$_3$), 1.38 (s, 3 H, 10-CH$_3$), 4.26 (t, J=5.7 Hz, 1 H, 1'-H), 6.06 (dd, J=3.9 Hz, 1 H, 3-H).

(1R,1'S,6S,9R)6,10,10-trimethyl-2-(1-hydroxybutyl)-11-oxatricyclo[7.2.1.0$^{1,6}$]dodec-2-ene: Oil, $[\alpha]_D^{10}$ +50° (c=0.05, chloroform).

MS: 278 (M+, 17), 245 (25), 235 (85), 217 (60), 41 (100); $^1$H NMR (CDCl$_3$, δ): 0.91 (s, 3 H, 6-CH$_3$), 0.92 (t, J=7.2 Hz, 3 H, 3'-CH$_3$/2R), 1.26 (s, 3 H, 10-CH$_3$), 1.37 (s, 3 H, 10-CH$_3$), 4.15 (dd, J=7.9, 5.5 Hz, 1 H, 1'-H), 5.94 (dd, J=3.9, 3.6 Hz, 1 H, 3-H).

EXAMPLE 28

(1R,6S,9R)6,10,10-Trimethyl-2-butanoyl-11-oxatricyclo[7.2.1.0$^{1,6}$]dodec-2-ene

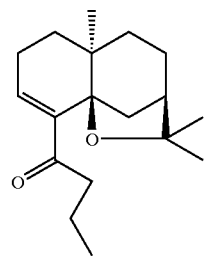

14 mg (0.065 mmol) of PCC was added into a solution of 9 mg (0.032 mmol) of (1R,1'R,6S,9R)6,10,10-trimethyl-2-(1-hydroxybutyl)-11-oxatricyclo[7.2.1.0$^{1,6}$]dodec-2-ene in 2 mL of methylene chloride and the reaction mixture was stirred at room temperature for 5 hours, then filtered through celite, after of added 5 mL of ether, the filtrate was concentrated and purified by column chromatography to give 6 mg of title product, yield 67%.

MS: 277 (M+1, 10), 261 (15), 243 (8), 233 (20), 218 (82), 200 (95), 157 (100); $^1$H NMR (CDCl$_3$, δ): 0.91 (t, J=7.2 Hz, 3 H, 3'-CH$_3$/2R), 0.92 (s, 3 H, 6-CH$_3$), 1.34 (s, 3 H, 10-CH$_3$), 1.35 (s, 3 H, 10-CH$_3$), 2.60 (tq, J=7.1, 2.8 Hz, 2 H 2'-H/2R) 4.15 (dd, J=7.9, 5.5 Hz, 1 H, 1'-H), 6.65 (dd, J=3.9, 3.6 Hz, 1 H, 3-H).

EXAMPLE 29

(1R,6S,9R)6,10,10-Trimethyl-2-(3-oxobutyl)-11-oxatricyclo[7.2.1.0$^{1,6}$]dodec-2-ene

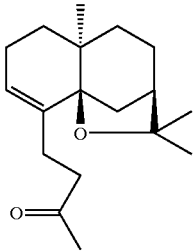

Step A: (1R,6S,9R)6,10,10-Trimethyl-2-(3-oxopropyl)-11-oxatricyclo[7.2.1.0$^{1,6}$]dodec-2-ene

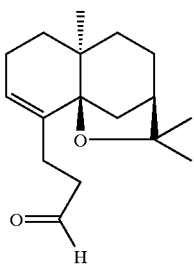

300 mg (1.39 mmol) of PCC was added to a solution of 100 mg (0.38 mmol) of (1R,6S,9R)6,10,10-trimethyl-2-(3-hydroxypropyl)-11-oxatricyclo[7.2.1.0$^{1,6}$]dodec-2-ene from example 12 in 15 ml of methylene chloride and the reaction mixture was stirred at room temperature for 3 hours, then was added 15 mL of ether. After filtration, the filtrate was concentrated to give 90 mg of crude product.

Step B: (1R,3'R,6S,9R)6,10,10-Trimethyl-2-(3-hydroxypropyl)-11-oxatricyclo[7.2.1.0$^{1,6}$]dodec-2-ene

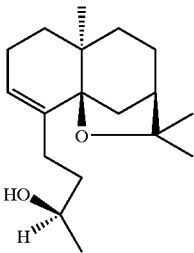

and (1R,3'S,6S,9R)6,10,10-Trimethyl-2-(3-hydroxypropyl)-11-oxatricyclo[7.2.1.0$^{1,6}$]dodec-2-ene

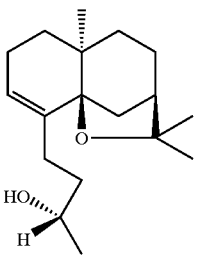

A mixture of the crude compound obtained in the above step A in 5 mL of ether was added to the Grignard reagent prepared from 284 mg (2 mmol) of methyl iodide and 60 mg (2.5 mmol) of magnesium in 10 mL of ether, and the reaction mixture was stirred at room temperature for 10 min, then quenched with saturated ammonium chloride solution, washed with brine, dried and evaporated to give crude product.

Step C: (1R,6S,9R)6,10,10-Trimethyl-2-(3-oxobutyl)-11-oxatricyclo[7.2.1.0$^{1,6}$]dodec-2-ene To the mixture of the crude product from the step B in 12 mL of methylene chloride was added 250 mg (1.16 mmol) of PCC, and the reaction mixture was stirred at room temperature for 3 hours, then 15 mL of ether was added, and filtered through celite. After concentration, the crude product was purified by column chromatography to give 40 mg of product, yield 38% (three steps).

White solid, mp 59–62° C., $[\alpha]_D^{10}$+17.1° (c=0.21, chloroform). MS: 277 (M+1, 100), 259 (90), 219 (18), 203 (24); $^1$H NMR (CDCl$_3$, δ): 0.90 (s, 3 H, 6-CH$_3$), 1.25 (s, 3 H, 10-CH$_3$), 1.37 (s, 3 H, 10-CH$_3$), 2.16 (s, 3 H, 4'-CH$_3$/2R), 2.32 (m 2 H, 1'-H/2R), 2.57 (m, 2 H, 2'-H/2R), 5.55 (br.s, 1 H, 3-H).

EXAMPLE 30

(1S,2R,3S,6R,9R)2,6,10,10-Tetramethyl-3-hydroxy-11-oxatricyclo[7.2.1.0$^{1,6}$]dodecane

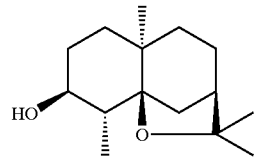

A solution of 60 mg (0.26 mmol) of (1S,2S,3S,6R,9R)6,10,10-trimethyl-2,3-epoxy-11-oxatricyclo[7.2.1.0$^{1,6}$]dodecane and 5 mL of ether was added to the Grignard reagent prepared from 26 mg (1.1 mmol) of magnesium and 142 mg (1 mmol) of methyl iodide, and the reaction mixture was stirred at room temperature for 15 min. then worked up. The crude product was purified by column chromatography to give 27 mg of product, yield 60%.

White solid, mp 76–77° C., $[\alpha]_D^{10}$–86.9° (c=0.16, chloroform). MS: 223 (M-15, 50), 205 (22), 177 (15), 163 (38), 147 (100); $^1$H NMR (CDCl$_3$, δ): 1.24 (s, 3 H, 6-CH$_3$), 1.31 (s, 3 H, 10-CH$_3$), 1.40 (s, 3 H, 10-CH$_3$), 4.19 (br.s, 1 H, 3-H).

EXAMPLE 31

(1S,2R,6R,9R)2,6,10,10-Tetramethyl-11-oxatricyclo[7.2.1.0$^{1,6}$]dodec-3-ene

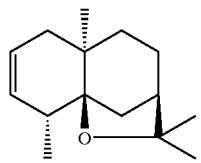

0.3 mL of thionyl chloride was added to a solution of 20 mg (0.082 mmol) of (1S,2R,3S,6R,9R)2,6,10,10-tetramethyl-3-hydroxy-11-oxatricyclo[7.2.1.0$^{1,6}$]dodecane from example 30 in 2 mL of pyridine cooled with ice-salt mixture, and the reaction mixture was stirred for 1.5 hours.

After work-up, the crude product was purified by column chromatography to give 14 mg of product, yield 76%.

Oil, $[\alpha]_D^{10}$+13.8° (c=0.16, chloroform). MS: 205 (M-15, 58), 187 (30), 147 (50), 41 (100); $^1$H NMR (CDCl$_3$, δ): 0.93 (s, 3 H, 6-CH$_3$), 1.22 (s, 3 H, 10-CH$_3$), 1.35 (s, 3 H, 10-CH$_3$), 5.43 (d, J=9.7 Hz, 1 H, 3-H), 5.83 (d, J=9.7 Hz, 1 H, 4-H).

EXAMPLE 32

(1S,6R,9R)3,6,10,10-Tetramethyl-11-oxatricyclo [7.2.1.0$^{1,6}$]dodec-2-ene

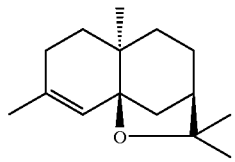

Step A: (6R/S,9R)6-Methyl-9-(1-hydroxyisopropyl)-bicyclo [4.4.0]dec-1-ene-3-one

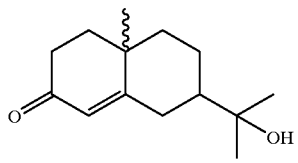

1.2 g (5.87 mmol) of (6R/S,9R)6-Methyl-9-(1-methylvinyl)-bicyclo[4.4.0]dec-1-ene-3-one from step C of preparation A was dissolved in 20 mL of formic acid and added to 4 mL of 5% sulfuric acid solution. The reaction mixture was stirred at room temperature for 2 days, in refrigerator for 3 days, then neutralized with K$_2$CO$_3$ with cooling, and extracted with ethyl acetate. The extract was washed with saturated NaHCO$_3$ solution and brine, dried, and evaporated. The residue was purified by column chromatography (silica gel, petroleum ether/ethyl acetate 5/1) to give 500 mg of product as oil and 620 mg of recovered starting material, yield 39%.

MS: 204 (M-18, 5), 176 (3), 164 (15), 149 (16), 91 (10), 59 (100); $^1$H NMR (CDCl$_3$, δ): 1.16 (s, 3 H, 6-CH$_3$), 1.20 (s, 3 H, 10-CH$_3$), 1.26 (s, 3 H, 10-CH$_3$), 5.81 (s, 1 H, 2-H) IR: 3431, 2966, 2929, 1660, 1650, 1618, 1464, 1379, 1178.

Step B: (3R/S,6R/S,9R)3,6-Dimethyl-9-(1-hydroxyisopropyl)-3-hydroxy-bicyclo[4.4.0]dec-1-ene

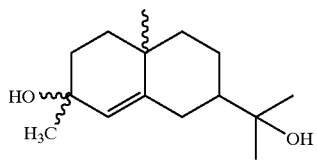

74 mg (0.333 mmol) of the product of step A was dissolved in 5 mL of ether and added to the Grignard reagent prepared from 284 mg (2 mmol) methyl iodide and 60 mg (2.5 mmol) of magnesium in 10 mL of ether, and the reaction mixture was stirred at room temperature for 1 hour, then quenched with saturated ammonium chloride solution. The ether layer was washed with brine, dried, and evaporated to give crude product.

Step C: (1S,6R,9R)3,6,10,10-Tetramethyl-11-oxatricyclo [7.2.1.0$^{1,6}$]dodec-2-ene A mixture of 25 μL of concentrated HCl in 25 mL of methanol was added to the crude product from the step B, and the reaction mixture was stirred at room temperature for 5 min. then neutralized with 10% NaOH solution. After evaporation, the residue was purified by column chromatography (silica gel, petroleum ether/ethyl acetate 60/1) to give 41 mg of product, yield 56% (two steps).

White solid,: mp 38–39° C., $[\alpha]_D^{10}$45.8° (c=0.47, chloroform). MS: 220 (M+, 15), 205 (50), 187 (14), 162 (31), 147 (50), 31 (100); $^1$H NMR (CDCl$_3$, δ): 0.90 (s, 3 H, 6-CH$_3$), 1.21 (s, 3 H, 10-CH$_3$), 1.33 (s, 3 H, 10-CH$_3$), 1.37 (s, 3 H, 3-CH3), 5.16 (s, 1 H, 2-H).

EXAMPLE 33

(1S,6R,9R)6,10,10-Trimethyl-3-butyl-11-oxatricyclo [7.2.1.0$^{1,6}$]dodec-2-ene

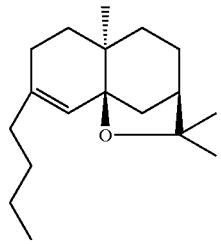

The compound was prepared according to the procedures described in example 32, using butyl bromide instead of methyl iodide.

Oil, $[\alpha]_D^{17}$+40.18° (c=1.09, acetone). MS: 262 (M$^+$, 30), 247 (78), 220 (45), 204 (55), 189 (22), 147 (100), 105 (37), 91 (53), 82 (78); $^1$H NMR (CDCl$_3$, δ): 0.88 (t, J=7.2 Hz, 3 H, 3'-CH3/3R), 0.89 (s, 3 H, 6-CH$_3$), 1.20 (s, 3 H, 10-CH$_3$), 1.33 (s, 3 H, 10-CH$_3$), 5.13 (s, 1 H, 2-H).

Pharmacological Experiment

The compound of formula (I) showed good activity in animal models of anxiety such as elevated plus maze test and social interaction test on rats. In forced swimming test in mice, the compound also showed anti-depression activity. Compounds of formula (I) had low toxicity in a single dose toxicity test in mice. The compound used in the following pharmacological experiment is the compound of example 2, that is (1R,6S,9R)6,10,10-trimethyl-2-butyl-11-oxatricyclo [7.2.1.0$^{1,6}$]dodec-2-ene (thereafter referred as AF-5).

Anti-anxiety Activity Test of AF-5
1. Elevated Plus Maze Test on Rats

The elevated plus-maze test has been used by Pellow, S. And File, SE. for anti-anxiety model in rats. It is one of the most widely used models for anxiolytics. The elevated plus maze has two cross arms, one is an opened arm (50*10 cm, length, width), another is a closed arm (50×10×40 cm, length, width, height) and the maze is 50 cm above the floor during experiment. The rat for experiment is put on the opening at the cross point (10×10) of the two arms, and may freely choose to enter either opened or closed arm.

Wistar rats of 160±20 g body weight were used, and divided randomly into 8 groups, 12 in each group. Handling adaptability training was carried out one week before the experiment. In the experiment, AF-5 in 2% lecithin of the doses listed in Table 1 was given to rats which were fasted for 12 hours before experiment. After administration, the rat was put on the center opening of the elevated plus headed to opened arm, and times of entering the opened arm, total time of staying on the opened arm, and times of shuttling inside the closed arm were recorded. The compound for test is considered active if it can prolong the staying time in opened arm but does not reduce the times of shuttling.

Table 1. The dose-effect relation of AF-5 (ip, 5 min) in elevated plus maze test in rats ($\bar{x} \pm SD$)

TABLE 1

The dose-effect relation of AF-5 (ip, 5 min) in elevated plus maze test in rats ($\bar{x} \pm SD$)

| | control (2% lecithin) | AF-5 (mg/kg) | | | | | | |
|---|---|---|---|---|---|---|---|---|
| dose | — | 0.5 | 1 | 2 | 4 | 8 | 16 | 32 |
| n | 12 | 12 | 12 | 12 | 12 | 12 | 12 | 4 |
| total time of staying on the opened arm (sec. in 5 min.) | 64 ± 10 | 23 ± 21 | 25 + 17* | 36 ± 28** | 30 ± 30* | 14 ± 13 | 9.8 ± 9.0 | 9.6 ± 11 |
| Times of shuttling | 12 ± 0.4 | 2.5 ± 2.4 | 2.8 ± 2.0* | 2.8 ± 2.3* | 2.3 ± 1.1 | 1.3 ± 0.6 | 4.2 ± 1.8* | 3.0 ± 1.6* |

*P < 0.05,
**P < 0.01, compared with the control

The data in table 1 indicated that AF-5 has antianxiety activity with a wide dosage range.

TABLE 2

The time-effect relation of AF-5 (2 mg/kg, ip) in elevated plus maze test in rats ($\bar{x} \pm SE$)

| | Control (2% lecithin) | AF-5 | | | | |
|---|---|---|---|---|---|---|
| time | 5 minutes | 5 minutes | 15 minutes | 30 minutes | 60 minutes | 90 minutes |
| N | 12 | 12 | 12 | 12 | 12 | 12 |
| Time in opened arm | 2.1 ± 0.9 | 4.4 ± 1.6 | 6.1 ± 1.5* | 7.9 ± 3.4 | 20.8 ± 6.7** | 1.27 ± 3.6 |
| Times of shuttling | 3.4 ± 1.1 | 3.0 ± 0.8 | 4.1 ± 0.8 | 6.6 ± 2.0 | 5.6 ± 1.6 | 3.7 ± 0.9 |

*P < 0.05,
**P < 0.01, compared with the control
The data in table 2 indicated that AF-5 has fast and long lasting effect.

2. Social Interaction Test on Rats

The rats (Wistar, 160±20 g) for experiment were individually housed in chambers (55×55×40 cm), and handling adaptability and injection training were carried out twice a day 2 weeks before experiment. One day before experiment, the rats were weighed, labeled and grouped at random in pairs but still separated-until experiment. In experiment, 8 pairs of rats were given AF-5 in 2% lecithin (2% lecithin as control), and the total time of interaction was recorded including smelling, licking, leaning against, grabbing, chasing, biting, following, kicking, hitting etc. The experiment conditions were high illuminance with unfamiliar conditions (HU), low illuminance with unfamiliar conditions, high illuminance with familiar conditions and low illuminance with familiar conditions T-test was used to determine the significance between the test group and control group (Table 3, 4).

TABLE 3

Dose-effect relation of AF-5 (5 mg/kg) in social interaction test on rats (second, illuminance, unfamiliar conditions, HU). ($\bar{x} \pm SD$)

| | control (2% lecithin) | AF-5 (mg/kg) | | | | | |
|---|---|---|---|---|---|---|---|
| dose | — | 0.125 | 0.25 | 0.5 | 1.0 | 2.0 | 4.0 |
| n | 10 | 10 | 10 | 10 | 10 | 10 | 10 |
| 0–9 (minutes) | 131 ± 20 | 116 ± 30 | 137 ± 24 | 219 ± 57*** | 241 ± 64** | 195 ± 52* | 194 ± 33* |

*P < 0.05,
**P < 0.01,
***P < 0.001, compared with the control

TABLE 4

Time-effect relation of AF-5 (2 mg/kg, ip) in social interaction test in rats (second, illuminance, unfamiliar conditions, HU) ($\bar{x} \pm SD$)

| | control (2% lecithin) | AF-5 | | | | |
|---|---|---|---|---|---|---|
| time | 5 minutes | 5 minutes | 15 minutes | 30 minutes | 60 minutes | 90 minutes |
| n | 12 | 12 | 12 | 12 | 12 | 12 |
| interaction time (sec. in 9 min) | 103 ± 14 | 98 ± 11 | 143 ± 9** | 103 ± 14 | 166 ± 21* | 112 ± 8 |

*P < 0.05,
**P < 0.01, compared with the control

The Anti-depression Activity of AF-5

The experiment used Kunming mice of China, male, 18–21 g of body weight. There were three dosing regimens (table 6) for the experiment, that is 1) single dosage 1.5, 5, 15 mg/kg, tested 30 min after administration; 2) 0.5, 1.5, 5 mg/kg, three times a day (24, 5, 0.5 hours before experiment; 3) 5 mg/kg a day in one dosage, in successive 21 days, tested 0.5 hour after the last administration.

The water in experiment vessel was 12 cm in depth, 12.5 cm in diameter and kept at 26° C. Each mouse was put in the water and forced to swim for 6 min in which total immobile time in the last 4 min was recorded, and the significance between experiment group and control group was tested by T value (Table 5).

TABLE 5

Results of increasing mobile time in forced swimming test on mice in three regimens of AF-5: 1) single dosage; 2) three times a day; 3) one dosage a day in 21 successive days; saline as control, and fluoxetine (ip) as positive control. ($\bar{x} \pm SD$)

| group | methods of dosing | dose (mg/kg) | n | time of immobile phase (sec/4 min) |
|---|---|---|---|---|
| (1) single dosing of AF-5 | | | | |
| control | (P.O., 0.5 hr) | — | 10 | 95 ± 48 |
| AF-5 | (P.O., 0.5 hr) | 1.5 | 10 | 93 ± 39 |
| | | 5.0 | 10 | 101 ± 52 |
| | | 15.0 | 10 | 97 ± 43 |
| (2) three times a day | | | | |
| control | (P.O., ×3 times) | — | 10 | 111 ± 46 |
| AF-5 | (P.O., ×3 times, 24, 5, 0.5 hours before experiment) | 0.5 | 10 | 90 ± 25 |
| | | 1.5 | 9 | 60 ± 30* |
| | | 5.0 | 10 | 83 ± 35 |
| | | 15.0 | 10 | 74 ± 41 |

TABLE 5-continued

Results of increasing mobile time in forced swimming test on mice in three regimens of AF-5: 1) single dosage; 2) three times a day; 3) one dosage a day in 21 successive days; saline as control, and fluoxetine (ip) as positive control. ($\bar{x} \pm SD$)

| group | methods of dosing | dose (mg/kg) | n | time of immobile phase (sec/4 min) |
|---|---|---|---|---|
| | (3) one dosage a day in successive 21 days | | | |
| control | (P.O., 0.5 hr) | — | 10 | 150 ± 42 |
| AF-5 | (P.O., s.i.d. × 21 days) | 5.0 | 10 | 84 ± 41** |
| | | 7.5 | 10 | 69 ± 45** |
| | | 15.0 | 10 | 92 ± 66** |

*P < 0.05,
**P < 0.01, compared with the control

The results from Table 5 indicated that single dosing of AF-5 (1.5, 5, and 15 mg/kg) did not prolong the time of mobile phase (P>0.05 vs. control); administration three times a day showed significance in the 1.5 mg/kg group, whereas the 0.5 and 5 mg/kg groups did not show significance though prolonged the mobile time; administration in 21 successive days prolonged the mobile time significantly. Therefore AF-5 has anti-depression activity Single Dose Toxicity of AF-5

Intravenous injection of AF-5 500 mg in mice showed effect of calming, lying down, decreasing alarm reaction and without other abnormal reactions. One week alive rate was 100%. The possible durable dosage was 2.4 g/kg by P.O. and two week alive rate was 100% at this dosage. Therefore, AF-5 is a anxiolytic with low toxicity and high safety coefficient.

What is claimed is:

1. A compound of formula (I),

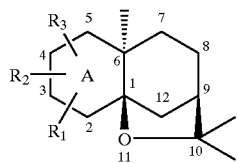

(I)

wherein a double bond is present at position 2–3 of the A ring, $R_1$ is located at position 2 or 3 of the A ring and is a $C_{2-6}$ straight or branched chain alkyl wherein said alkyl is optionally substituted with hydroxyl, carbonyl, benzyl, or halogen-substituted benzyl, and $R_2$ and $R_3$ are hydrogen; or stereoisomers thereof.

2. A compound of claim 1, of formula (Ia),

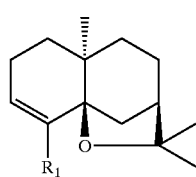

(Ia)

wherein $R_1$ is butyl; or stereoisomers thereof.

3. A compound of claim 1, wherein said compound is (1R,6S,9R)6,10,10-Trimethyl-2-propyl-11-oxatricyclo[7.2.1.0$^{1,6}$]dodec-2-ene;

(1R,6S,9R)6,10,10-Trimethyl-2-butyl-11-oxatricyclo[7.2.1.0$^{1,6}$]dodec-2-ene;

(1R,6S,9R)6,10,10-Trimethyl-2-pentyl-11-oxatricyclo[7.2.1.0$^{1,6}$]dodec-2-ene;

(1R,6S,9R)6,10,10-Trimethyl-2-hexyl-11-oxatricyclo[7.2.1.0$^{1,6}$]dodec-2-ene;

(1R,6S,9R)6,10,10-Trimethyl-2-isopentyl-11-oxatricyclo[7.2.1.0$^{1,6}$]dodec-2-ene;

(1R,6S,9R)6,10,10-Trimethyl-2-benzyl-11-oxatricyclo[7.2.1.0$^{1,6}$]dodec-2-ene;

(1R,6S,9R)6,10,10-Trimethyl-2-(4-fluorobenzyl)-11-oxatricyclo[7.2.1.0$^{1,6}$]dodec-2-ene;

(1R,6S,9R)6,10,10-Trimethyl-2-(3-hydroxypropyl)-11-oxatricyclo[7.2.1.0$^{1,6}$]dodec-2-ene;

(1R,1'R,6S,9R)6,10,10-Trimethyl-2-(1-hydroxybutyl)-11-oxatricyclo[7.2.1.0$^{1,6}$]dodec-2-ene;

(1R1'S,6S,9R)6,10,10-Trimethyl-2-(1-hydroxybutyl)-11-oxatricyclo[7.2.1.0$^{1,6}$]dodec-2-ene;

2-Butyryl(1R,6S,9R)6,10,10-Trimethyl-11-oxatricyclo[7.2.1.0$^{1,6}$]dodec-2-ene; or (1S,6R,9R)6,10,10-Trimethyl-3-butyl-11-oxatricyclo[7.2.1.0$^{1,6}$]dodec-2-ene.

4. A pharmaceutical composition comprising, at least one compound of formula (I) or its stereoisomer of claim 1 as an active ingredient, and a conventional pharmaceutical carrier or excipient.

5. A pharmaceutical composition comprising, at least one compound of formula (I) or its stereoisomer of claim 2 as an active ingredient, and a conventional pharmaceutical carrier or excipient.

6. A pharmaceutical composition of claim 4, wherein said active ingredient is at least one compound selected from the group consisting of:

(1R,6S,9R)6,10,10-Trimethyl-2-propyl-11-oxatricyclo[7.2.1.0$^{1,6}$]dodec-2-ene;

(1R,6S,9R)6,10,10-Trimethyl-2-butyl-11-oxatricyclo[7.2.1.0$^{1,6}$]dodec-2-ene;

(1R,6S,9R)6,10,10-Trimethyl-2-pentyl-11-oxatricyclo[7.2.1.0$^{1,6}$]dodec-2-ene;

(1R,6S,9R)6,10,10-Trimethyl-2-hexyl-11-oxatricyclo[7.2.1.0$^{1,6}$]dodec-2-ene;

(1R,6S,9R)6,10,10-Trimethyl-2-isopentyl-11-oxatricyclo[7.2.1.0$^{1,6}$]dodec-2-ene; (1R,6S,9R)6,10,10-Trimethyl-2-benzyl-11-oxatricyclo[7.2.1.0$^{1,6}$]dodec-2-ene;

(1R,6S,9R)6,10,10-Trimethyl-2-(4-fluorobenzyl)-11-oxatricyclo[7.2.1.0$^{1,6}$]dodec-2-ene;

(1R,6S,9R)6,10,10-Trimethyl-2-(3-hydroxypropyl)-11-oxatricyclo[7.2.1.0$^{1,6}$]dodec-2-ene;

(1R,1'R,6S,9R)6,10,10-Trimethyl-2-(1-hydroxybutyl)-11-oxatricyclo[7.2.1.0$^{1,6}$]dodec-2-ene;

(1R,1'S,6S,9R)6,10,10-Trimethyl-2-(1-hydroxybutyl)-11-oxatricyclo[7.2.1.0$^{1,6}$]dodec-2-ene;

2-Butyryl(1R,6S,9R)6,10,10-Trimethyl-11-oxatricyclo[7.2.1.0$^{1,6}$]dodec-2-ene; and (1S,6R,9R)6,10,10-Trimethyl-3-butyl-11-oxatricyclo[7.2.1.0$^{1,6}$]dodec-2-ene.

7. A method for the treatment of anxiety and/or depression, comprising administering at least one compound of formula (I),

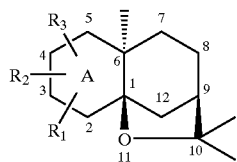

(I)

wherein a double bond is present at position 2–3 of the A ring,
- $R_1$ is located at position 2 or 3 of the A ring and is a $C_{2-6}$ straight or branched chain alkyl wherein said alkyl is optionally substituted with hydroxyl, carbonyl, benzyl, or halogen-substituted benzyl, and
- $R_2$ and $R_3$ are hydrogen; or stereoisomers thereof, in effective amount for treatment of anxiety and/or depression to mammals.

8. The method of claim 7 wherein said mammal is a human being.

9. The method for treatment of anxiety and/or depression of claim 7, wherein said at least one compound is a compound of formula (Ia),

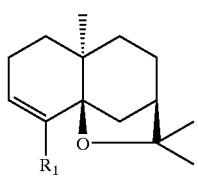

(Ia)

wherein $R_1$ is butyl; or stereoisomers thereof.

10. The method of claim 9, wherein said mammal is a human being.

11. The method for the prevention and/or treatment of anxiety and/or depression of claim 7, wherein said at least one compound is:
- (1R,6S,9R)6,10,10-Trimethyl-2-propyl-11-oxatricyclo [7.2.1.0$^{1,6}$]dodec-2-ene;
- (1R,6S,9R)6,10,10-Trimethyl-2-butyl-11-oxatricyclo [7.2.1.0$^{1,6}$]dodec-2-ene;
- (1R,6S,9R)6,10,10-Trimethyl-2-pentyl-11-oxatricyclo [7.2.1.0$^{1,6}$]dodec-2-ene;
- (1R,6S,9R)6,10,10-Trimethyl-2-hexyl-11-oxatricyclo [7.2.1.0$^{1,6}$]dodec-2-ene;
- (1R,6S,9R)6,10,10-Trimethyl-2-isopentyl-11-oxatricyclo [7.2.1.0$^{1,6}$]dodec-2-ene;
- (1R,6S,9R)6,10,10-Trimethyl-2-benzyl-11-oxatricyclo [7.2.1.0$^{1,6}$]dodec-2-ene;
- (1R,6S,9R)6,10,10-Trimethyl-2-(4-fluorobenzyl)-11-oxatricyclo[7.2.1.0$^{1,6}$]dodec-2-ene;
- (1R,6S,9R)6,10,10-Trimethyl-2-(3-hydroxypropyl)-11-oxatricyclo[7.2.1.0$^{1,6}$]dodec-2-ene;
- (1R,1'R,6S,9R)6,10,10-Trimethyl-2-(1-hydroxybutyl)-11-oxatricyclo[7.2.1.0$^{1,6}$]dodec-2-ene;
- (1R1'S,6S,9R)6,10,10-Trimethyl-2-(1-hydroxybutyl)-11-oxatricyclo[7.2.1.0$^{1,6}$]dodec-2-ene;
- 2-Butyryl(1R,6S,9R)6,10,10-Trimethyl-11-oxatricyclo [7.2.1.0$^{1,6}$]dodec-2-ene; or
- (1S,6R,9R)6,10,10-Trimethyl-3-butyl-11-oxatricyclo [7.2.1.0$^{1,6}$]dodec-2-ene.

12. The method of claim 11, wherein said mammal is a human being.

13. A method for the treatment of anxiety and/or depression, comprising administering a composition comprising at least one compound of formula (I),

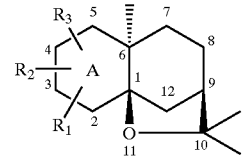

(I)

wherein a double bond is present at position 2–3 of the A ring,
- $R_1$ is located at position 2 or 3 of the A ring and is a $C_{2-6}$ straight or branched chain alkyl wherein said alkyl is optionally substituted with hydroxyl, carbonyl, benzyl, or halogen-substituted benzyl, and
- $R_2$ and $R_3$ are hydrogen; or stereoisomers thereof; as an active ingredient, and a conventional pharmaceutical carrier or excipient in effective amount for treatment of anxiety and/or depression to mammals.

14. The method of claim 13, wherein said mammal is a human being.

15. The method for the treatment of anxiety and/or depression of claim 13, wherein said at least one compound is a compound of formula (Ia),

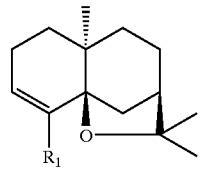

(Ia)

wherein $R_1$ is butyl; or stereoisomers thereof.

16. The method of claim 15, wherein said mammal is a human being.

17. A method for the treatment of anxiety and/or depression of claim 13, wherein said at least one compound is:
- (1R,6S,9R)6,10,10-Trimethyl-2-propyl-11-oxatricyclo [7.2.1.0$^{1,6}$]dodec-2-ene;
- (1R,6S,9R)6,10,10-Trimethyl-2-butyl-11-oxatricyclo [7.2.1.0$^{1,6}$]dodec-2-ene;
- (1R,6S,9R)6,10,10-Trimethyl-2-pentyl-11-oxatricyclo [7.2.1.0$^{1,6}$]dodec-2-ene;
- (1R,6S,9R)6,10,10-Trimethyl-2-hexyl-11-oxatricyclo [7.2.1.0$^{1,6}$]dodec-2-ene;
- (1R,6S,9R)6,10,10-Trimethyl-2-isopentyl-11-oxatricyclo [7.2.1.0$^{1,6}$]dodec-2-ene;
- (1R,6S,9R)6,10,10-Trimethyl-2-benzyl-11-oxatricyclo [7.2.1.0$^{1,6}$]dodec-2-ene;
- (1R,6S,9R)6,10,10-Trimethyl-2-(4-fluorobenzyl)-11-oxatricyclo[7.2.1.0$^{1,6}$]dodec-2-ene;
- (1R,6S,9R)6,10,10-Trimethyl-2-(3-hydroxypropyl)-11-oxatricyclo[7.2.1.0$^{1,6}$]dodec-2-ene;
- (1R,1'R,6S,9R)6,10,10-Trimethyl-2-(1-hydroxybutyl)-11-oxatricyclo[7.2.1.0$^{1,6}$]dodec-2-ene;

(1R1'S,6S,9R)6,10,10-Trimethyl-2-(1-hydroxybutyl)-11-oxatricyclo[7.2.1.0$^{1,6}$]dodec-2-ene;

2-Butyryl(1R,6S,9R)6,10,10-Trimethyl-11-oxatricyclo[7.2.1.0$^{1,6}$]dodec-2-ene; or (1S,6R,9R)6,10,10-Trimethyl-3-butyl-11-oxatricyclo[7.2.1.0$^{1,6}$]dodec-2-ene.

18. The method of claim 17, wherein said mammal is a human being.

19. A process of preparation of compound of formula (Ia)

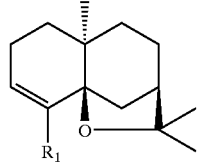

(Ia)

wherein $R_1$ is butyl; or stereoisomers thereof, comprising (i) reacting compound of formula (1) with $R_1X$ in basic medium and organic solvent wherein $R_1$ is butyl and X is a halogen,

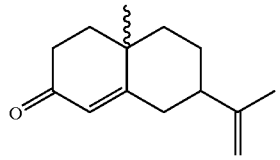

(1)

to form compounds of formula (2)

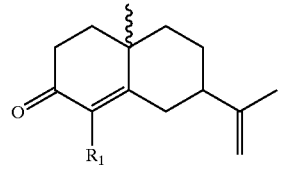

(2)

(ii) reaction of compound of formula (2) obtained from (i) with organic peracid to form compound of formula (3),

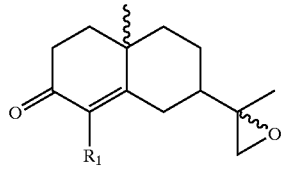

(3)

(iii) reduction of compound of formula (3) with reducing agent to form compounds of formula (4),

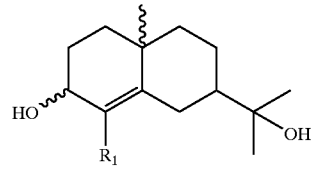

(4)

(iv) cyclization of compound of formula (4) in acidic medium to produce compound of formula (Ia).

* * * * *